(12) United States Patent
Chi Sing et al.

(10) Patent No.: US 8,517,907 B2
(45) Date of Patent: Aug. 27, 2013

(54) EXPANDABLE BRACHYTHERAPY APPARATUS AND METHODS FOR USING THEM

(75) Inventors: Eduardo Chi Sing, Dana Point, CA (US); Tommy G. Nguyen, Irvine, CA (US); George D. Hermann, Portola Valley, CA (US); Than Nguyen, Fountain Valley, CA (US); Doug S. Sutton, Pacifica, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 1114 days.

(21) Appl. No.: 12/277,286

(22) Filed: Nov. 24, 2008

(65) Prior Publication Data

US 2009/0156882 A1    Jun. 18, 2009

Related U.S. Application Data

(60) Provisional application No. 61/014,071, filed on Dec. 16, 2007.

(51) Int. Cl.
*A61M 36/12* (2006.01)

(52) U.S. Cl.
USPC ........................... 600/7; 600/1; 600/3

(58) Field of Classification Search
USPC .................. 600/7, 1, 3; 604/508, 509, 510, 604/107, 108, 109, 104, 105, 106
See application file for complete search history.

(56) References Cited

U.S. PATENT DOCUMENTS

| | | |
|---|---|---|
| 3,060,924 A | 10/1962 | Rush |
| 3,750,653 A | 8/1973 | Simon |
| 3,968,803 A | 7/1976 | Hyman |
| 4,427,005 A | 1/1984 | Tener |
| 4,580,561 A | 4/1986 | Williamson |
| 4,706,652 A | 11/1987 | Horowitz |

(Continued)

FOREIGN PATENT DOCUMENTS

| | | |
|---|---|---|
| DE | 3921291 | 1/1991 |
| DE | 3924291 | 1/1991 |

(Continued)

OTHER PUBLICATIONS

PCT International Search Report for PCT/US2008/084587, Applicant: Cianna Medical, Inc., Forms PCT/ISA/220 and PCT/ISA/210, Nov. 24, 2008, 10 pages.

(Continued)

*Primary Examiner* — Christine Matthews
*Assistant Examiner* — Joshua D Lannu
(74) *Attorney, Agent, or Firm* — William A. English; Vista IP Law Group LLP

(57) ABSTRACT

Apparatus for delivering brachytherapy to a target tissue region includes an elongate body including a proximal end, a distal end sized for introduction into a tissue tract and carrying a plurality of elongate members including pathways for receiving a source of radiation. The elongate members are movable between collapsed and expanded configurations. During use, a tract is created through tissue, and the elongate body carrying the elongate members is advanced through the tract into a target location with the elongate members in the collapsed configuration. The elongate members are directed to the expanded configuration at the target location, and radiation is delivered to treat tissue at the target location, e.g., by introducing one or more radiation sources along the pathways.

23 Claims, 28 Drawing Sheets

(56) References Cited

U.S. PATENT DOCUMENTS

| | | | |
|---|---|---|---|
| 4,714,074 A | 12/1987 | Rey et al. | |
| 4,798,212 A | 1/1989 | Arana | |
| 4,936,823 A | 6/1990 | Colvin et al. | |
| 4,957,476 A | 9/1990 | Cano | |
| 4,976,680 A | 12/1990 | Hayman et al. | |
| 5,056,523 A | 10/1991 | Hotchkiss, Jr. et al. | |
| 5,106,360 A | 4/1992 | Ishiwara et al. | |
| 5,152,741 A | 10/1992 | Farnio | |
| 5,188,596 A * | 2/1993 | Condon et al. | 604/103.1 |
| 5,235,966 A | 8/1993 | Jamner | |
| 5,242,372 A | 9/1993 | Carol | |
| 5,279,565 A | 1/1994 | Klein et al. | |
| 5,302,168 A | 4/1994 | Hess | |
| 5,336,178 A | 8/1994 | Kaplan et al. | |
| 5,354,257 A | 10/1994 | Roubin et al. | |
| 5,411,466 A | 5/1995 | Hess | |
| 5,423,747 A | 6/1995 | Amano | |
| 5,429,605 A | 7/1995 | Richling et al. | |
| 5,484,384 A | 1/1996 | Fearnot | |
| 5,503,613 A | 4/1996 | Weinberger | |
| 5,509,900 A | 4/1996 | Kirkman | |
| 5,538,502 A | 7/1996 | Johnstone | |
| 5,540,659 A | 7/1996 | Teirstein | |
| 5,611,767 A | 3/1997 | Williams | |
| 5,653,683 A | 8/1997 | D'Andrea | |
| 5,678,572 A | 10/1997 | Shaw et al. | |
| 5,707,332 A | 1/1998 | Weinberger | |
| 5,713,828 A | 2/1998 | Coniglione | |
| 5,720,717 A | 2/1998 | D'Andrea | |
| 5,730,698 A | 3/1998 | Fischell et al. | |
| 5,782,740 A | 7/1998 | Schneiderman | |
| 5,840,008 A | 11/1998 | Klein et al. | |
| 5,843,163 A | 12/1998 | Wall | |
| 5,851,171 A | 12/1998 | Gasson | |
| 5,863,284 A | 1/1999 | Klein | |
| 5,882,291 A | 3/1999 | Bradshaw et al. | |
| 5,891,091 A | 4/1999 | Teirstein | |
| 5,910,102 A | 6/1999 | Hastings | |
| 5,913,813 A | 6/1999 | Williams et al. | |
| 5,916,143 A | 6/1999 | Apple et al. | |
| 5,931,774 A | 8/1999 | Williams et al. | |
| 5,938,582 A | 8/1999 | Ciamacco, Jr. et al. | |
| 5,942,209 A | 8/1999 | Leavitt et al. | |
| 5,976,106 A | 11/1999 | Verin et al. | |
| 6,013,019 A | 1/2000 | Fischell et al. | |
| 6,022,308 A | 2/2000 | Williams | |
| 6,030,333 A | 2/2000 | Sioshansi et al. | |
| 6,033,357 A | 3/2000 | Ciezki et al. | |
| 6,036,632 A | 3/2000 | Whitmore et al. | |
| 6,056,722 A | 5/2000 | Jayaraman | |
| 6,059,752 A | 5/2000 | Segal | |
| 6,071,263 A | 6/2000 | Kirkman | |
| 6,074,339 A | 6/2000 | Gambale et al. | |
| 6,083,148 A | 7/2000 | Williams | |
| 6,117,064 A | 9/2000 | Apple et al. | |
| 6,159,139 A | 12/2000 | Chiu | |
| 6,159,141 A | 12/2000 | Apple et al. | |
| 6,176,821 B1 | 1/2001 | Crocker et al. | |
| 9,179,766 | 1/2001 | Dickerson | |
| 6,196,996 B1 | 3/2001 | Teirstein | |
| 6,200,256 B1 | 3/2001 | Weinberger | |
| 6,200,257 B1 | 3/2001 | Winkler | |
| 6,213,976 B1 | 4/2001 | Trerotola | |
| 6,217,585 B1 | 4/2001 | Houser et al. | |
| 6,221,003 B1 | 4/2001 | Sierocuk et al. | |
| 6,221,030 B1 | 4/2001 | Avaltroni | |
| 6,234,951 B1 | 5/2001 | Hastings | |
| 6,238,374 B1 | 5/2001 | Winkler | |
| 6,258,099 B1 | 7/2001 | Mareiro et al. | |
| 6,261,320 B1 | 7/2001 | Tam et al. | |
| 6,264,599 B1 | 7/2001 | Slater et al. | |
| 6,264,631 B1 | 7/2001 | Willis et al. | |
| 6,267,775 B1 | 7/2001 | Clerc et al. | |
| 6,287,249 B1 | 9/2001 | Tam et al. | |
| 6,338,709 B1 | 1/2002 | Geoffrion et al. | |
| 6,358,195 B1 | 3/2002 | Green et al. | |
| 6,371,904 B1 | 4/2002 | Sirimanne et al. | |
| 6,413,204 B1 | 7/2002 | Winkler et al. | |
| 6,458,069 B1 | 10/2002 | Tam et al. | |
| 6,482,142 B1 | 11/2002 | Winkler et al. | |
| 6,482,178 B1 | 11/2002 | Andrews et al. | |
| 6,494,824 B1 | 12/2002 | Apple et al. | |
| 6,506,145 B1 | 1/2003 | Bradshaw et al. | |
| 6,508,784 B1 | 1/2003 | Shu | |
| 6,527,692 B1 | 3/2003 | Weinberger | |
| 6,527,693 B2 | 3/2003 | Munro, III et al. | |
| 6,540,656 B2 | 4/2003 | Fontayne et al. | |
| 6,540,734 B1 | 4/2003 | Chiu et al. | |
| 6,554,757 B1 | 4/2003 | Geitz | |
| 6,582,353 B1 | 6/2003 | Hastings et al. | |
| 6,589,158 B2 | 7/2003 | Winkler | |
| 6,592,548 B2 | 7/2003 | Jayaraman | |
| 6,607,476 B1 | 8/2003 | Barnhart | |
| 6,607,478 B2 | 8/2003 | Williams | |
| 6,616,678 B2 * | 9/2003 | Nishtala et al. | 606/198 |
| 6,638,206 B2 | 10/2003 | Green et al. | |
| 6,641,518 B2 | 11/2003 | Wolfson et al. | |
| 6,645,135 B1 | 11/2003 | Bhat | |
| 6,648,811 B2 | 11/2003 | Sierocuk et al. | |
| 6,659,933 B2 | 12/2003 | Asano | |
| 6,673,006 B2 | 1/2004 | Winkler | |
| 6,676,667 B2 | 1/2004 | Mareiro et al. | |
| 6,685,619 B2 | 2/2004 | Halpern et al. | |
| 6,692,460 B1 | 2/2004 | Jayaraman | |
| 6,699,170 B1 | 3/2004 | Crocker et al. | |
| 6,746,465 B2 | 6/2004 | Diederich et al. | |
| 6,752,752 B2 | 6/2004 | Geitz | |
| 6,910,999 B2 | 6/2005 | Chin et al. | |
| 6,923,754 B2 | 8/2005 | Lubock | |
| 6,955,641 B2 | 10/2005 | Lubock | |
| 7,041,047 B2 | 5/2006 | Gellman et al. | |
| 7,056,276 B2 | 6/2006 | Nakano et al. | |
| 7,105,016 B2 * | 9/2006 | Shiu et al. | 623/1.12 |
| 7,357,770 B1 | 4/2008 | Cutrer et al. | |
| 2001/0007071 A1 | 7/2001 | Koblish | |
| 2002/0016583 A1 | 2/2002 | Cragg | |
| 2002/0032359 A1 | 3/2002 | Geoffrion et al. | |
| 2002/0165427 A1 | 11/2002 | Yachia et al. | |
| 2003/0092957 A1 | 5/2003 | Scott et al. | |
| 2003/0114878 A1 | 6/2003 | Diederich et al. | |
| 2003/0158515 A1 | 8/2003 | Gonzalez et al. | |
| 2003/0163017 A1 | 8/2003 | Tam et al. | |
| 2003/0236443 A1 | 12/2003 | Cespedes et al. | |
| 2004/0006305 A1 | 1/2004 | Hebert et al. | |
| 2004/0068231 A1 | 4/2004 | Blondeau | |
| 2004/0087828 A1 | 5/2004 | Green et al. | |
| 2004/0116767 A1 | 6/2004 | Lebovic et al. | |
| 2004/0127765 A1 | 7/2004 | Seiler et al. | |
| 2004/0147877 A1 * | 7/2004 | Heuser | 604/165.02 |
| 2004/0172041 A1 * | 9/2004 | Gresham et al. | 606/108 |
| 2004/0260142 A1 | 12/2004 | Lovoi | |
| 2005/0061533 A1 | 3/2005 | Lovoi | |
| 2005/0075662 A1 | 4/2005 | Pederson et al. | |
| 2005/0080313 A1 | 4/2005 | Stewart et al. | |
| 2005/0090845 A1 | 4/2005 | Boyd | |
| 2005/0096647 A1 | 5/2005 | Steinke et al. | |
| 2005/0101823 A1 | 5/2005 | Linares et al. | |
| 2005/0101860 A1 | 5/2005 | Patrick et al. | |
| 2005/0124843 A1 | 6/2005 | Singh | |
| 2005/0182286 A1 | 8/2005 | Lubock | |
| 2005/0240074 A1 | 10/2005 | Lubock | |
| 2006/0014997 A1 * | 1/2006 | Kindlein et al. | 600/3 |
| 2006/0015166 A1 | 1/2006 | Kindlein et al. | |
| 2006/0020156 A1 | 1/2006 | Shukla | |
| 2006/0094923 A1 | 5/2006 | Mate | |
| 2006/0100475 A1 * | 5/2006 | White et al. | 600/3 |
| 2006/0116546 A1 | 6/2006 | Eng | |
| 2006/0173233 A1 | 8/2006 | Lovoi | |
| 2006/0173235 A1 | 8/2006 | Lim et al. | |
| 2006/0184192 A1 | 8/2006 | Markworth et al. | |
| 2006/0199990 A1 | 9/2006 | Rioux et al. | |
| 2006/0235365 A1 | 10/2006 | Terwilliger et al. | |
| 2006/0258895 A1 | 11/2006 | Maschke | |
| 2007/0106108 A1 | 5/2007 | Hermann | |

| | | | | | |
|---|---|---|---|---|---|
| 2007/0167664 | A1 | 7/2007 | Hermann et al. | | |
| 2007/0167665 | A1 | 7/2007 | Hermann | | |
| 2007/0167667 | A1 | 7/2007 | Lubock et al. | | |
| 2007/0191668 | A1 | 8/2007 | Lubock et al. | | |
| 2007/0270627 | A1* | 11/2007 | Cutrer et al. | ...... | 600/7 |
| 2008/0091055 | A1* | 4/2008 | Nguyen et al. | ...... | 600/7 |
| 2008/0221384 | A1 | 9/2008 | Chi Sing | | |

FOREIGN PATENT DOCUMENTS

| | | |
|---|---|---|
| EP | 0318447 B1 | 9/1994 |
| EP | 0390528 B1 | 1/1997 |
| EP | 0775505 | 5/1997 |
| EP | 0536888 B1 | 1/1998 |
| EP | 0906769 | 4/1999 |
| EP | 0955071 | 11/1999 |
| EP | 0884977 B1 | 4/2003 |
| EP | 0782410 B1 | 12/2003 |
| EP | 0955071 | 2/2004 |
| EP | 1402922 | 3/2004 |
| EP | 1405600 | 4/2004 |
| EP | 0808129 B1 | 5/2004 |
| EP | 1428477 | 6/2004 |
| EP | 1568397 | 8/2005 |
| WO | 00/59378 | 10/2000 |
| WO | 01/95808 | 12/2001 |
| WO | 03/077768 | 9/2003 |
| WO | 03/079907 | 10/2003 |
| WO | 2005037363 | 4/2005 |

OTHER PUBLICATIONS

PCT Written Opinion for PCT/US2008/084587, Applicant: Cianna Medical, Inc., Forms PCT/ISA/237, Nov. 24, 2008, 13 pages.

* cited by examiner

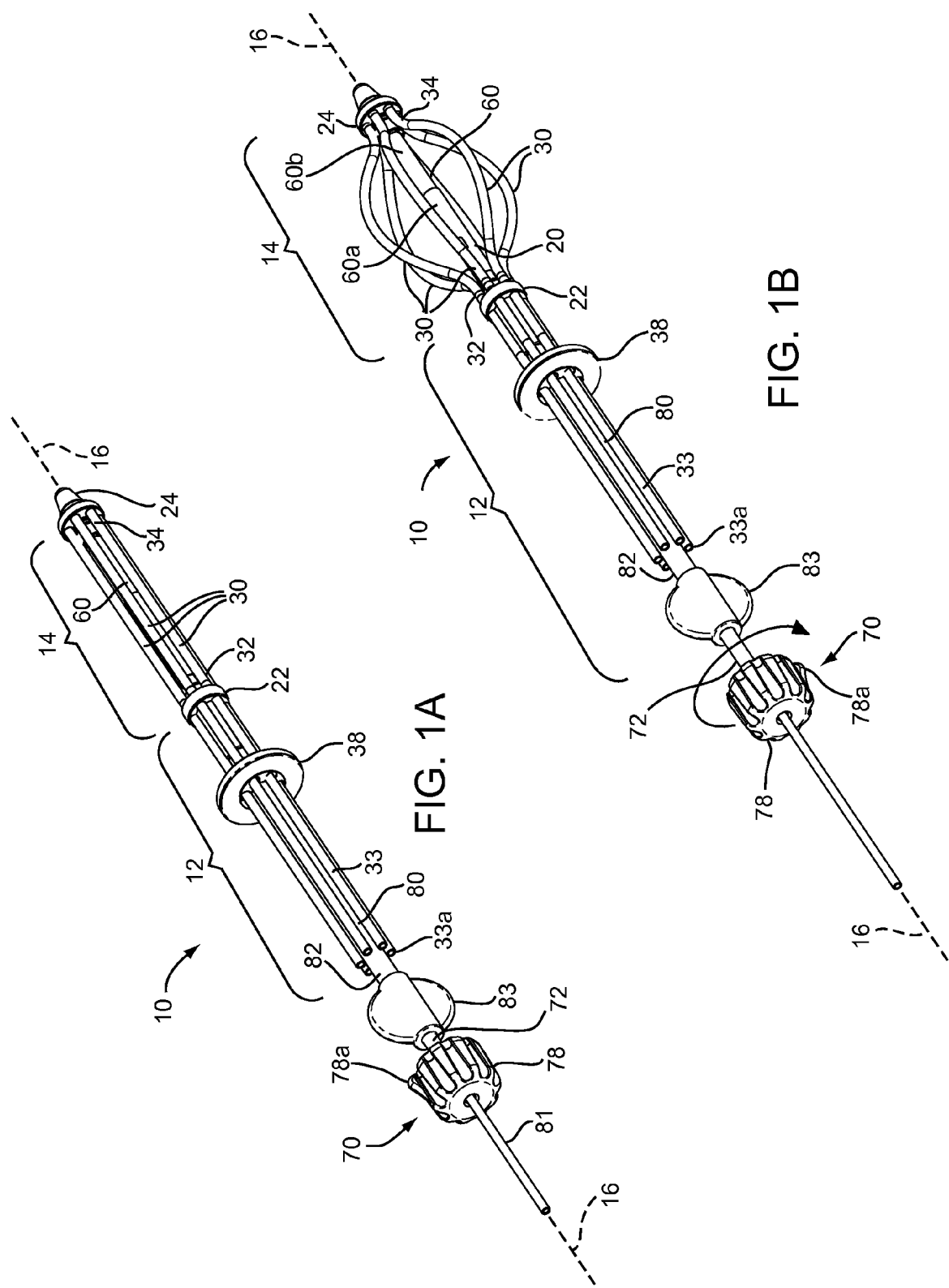

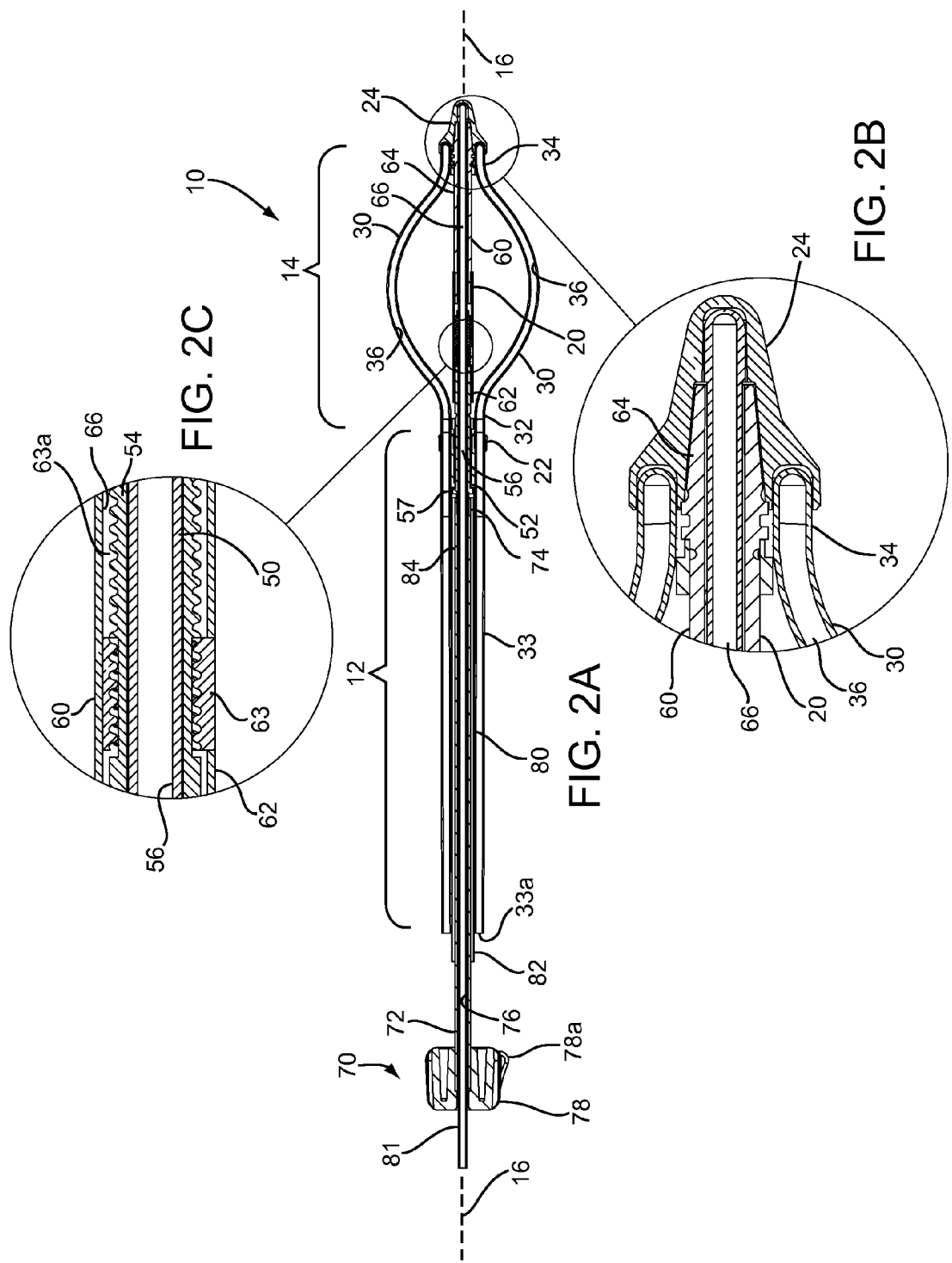

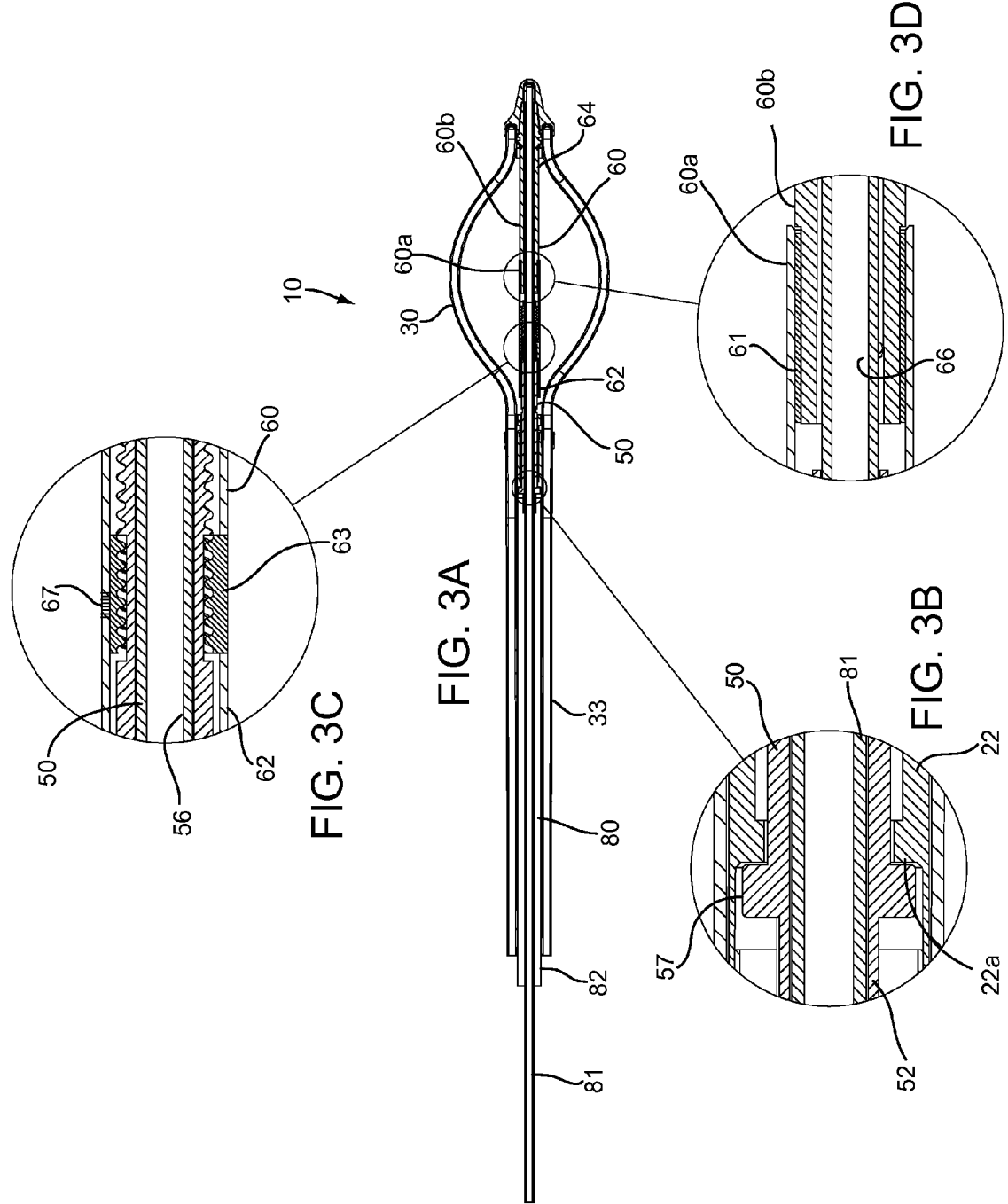

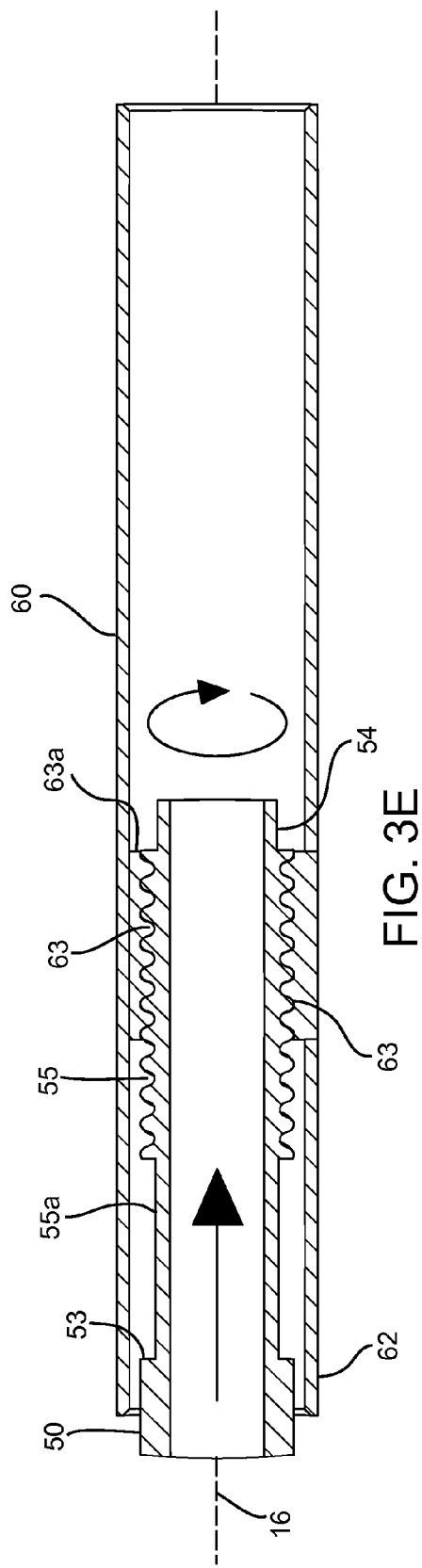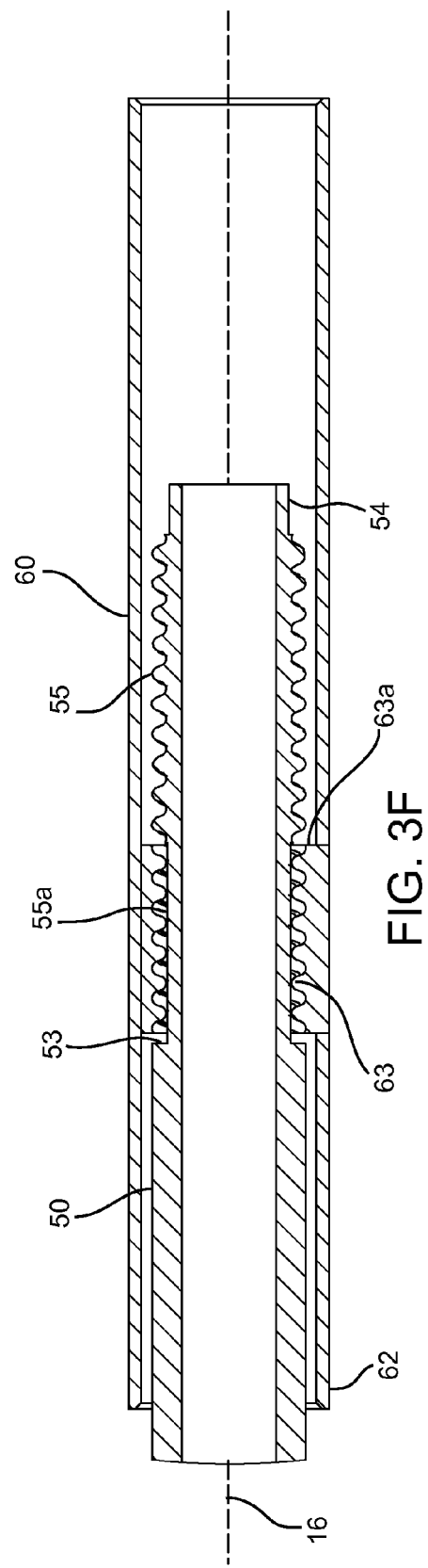

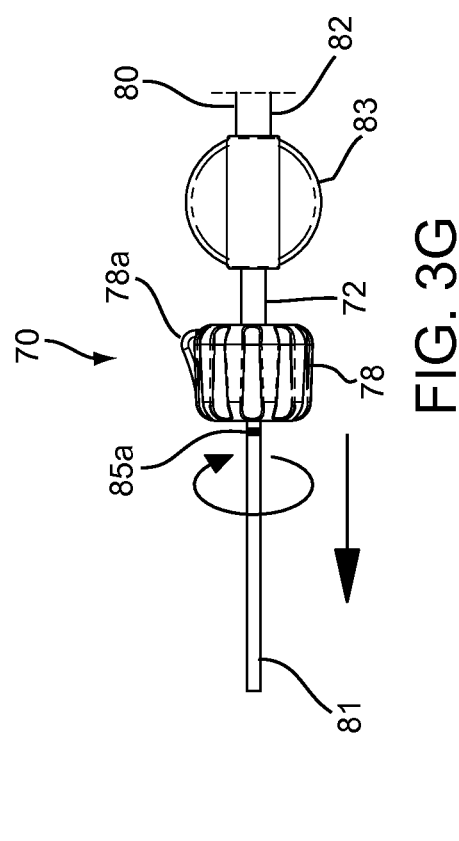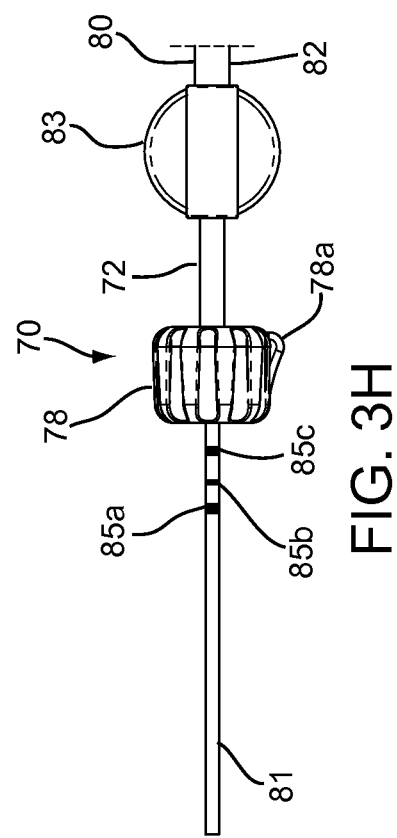

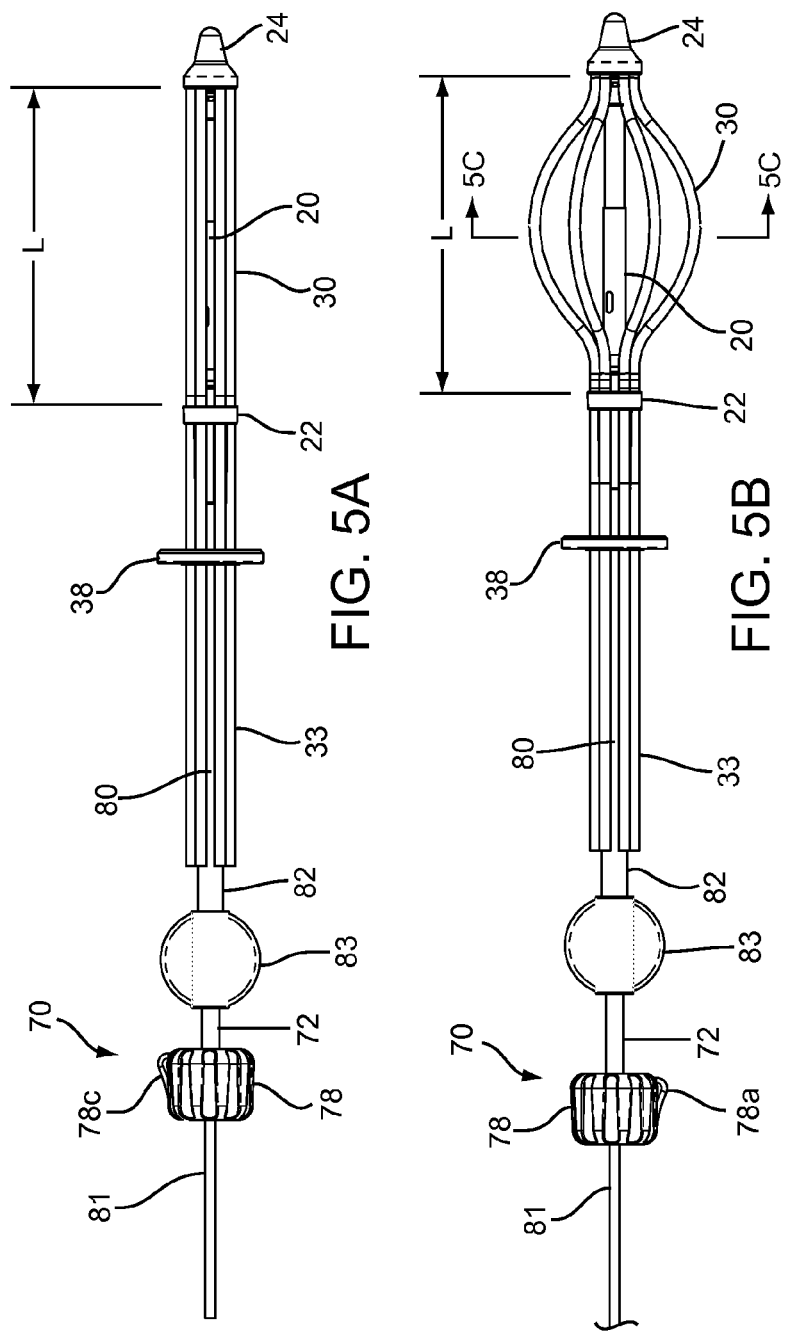

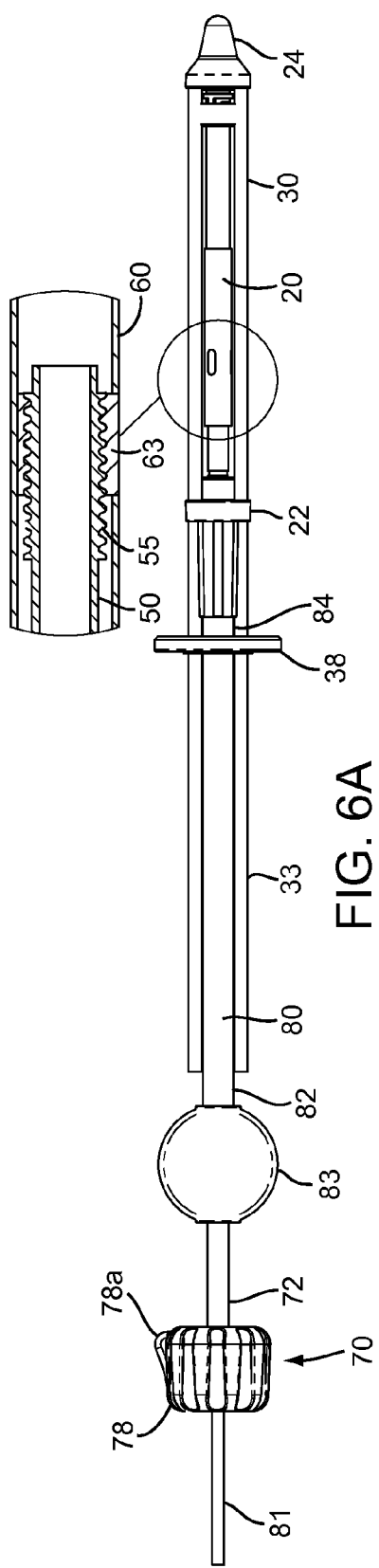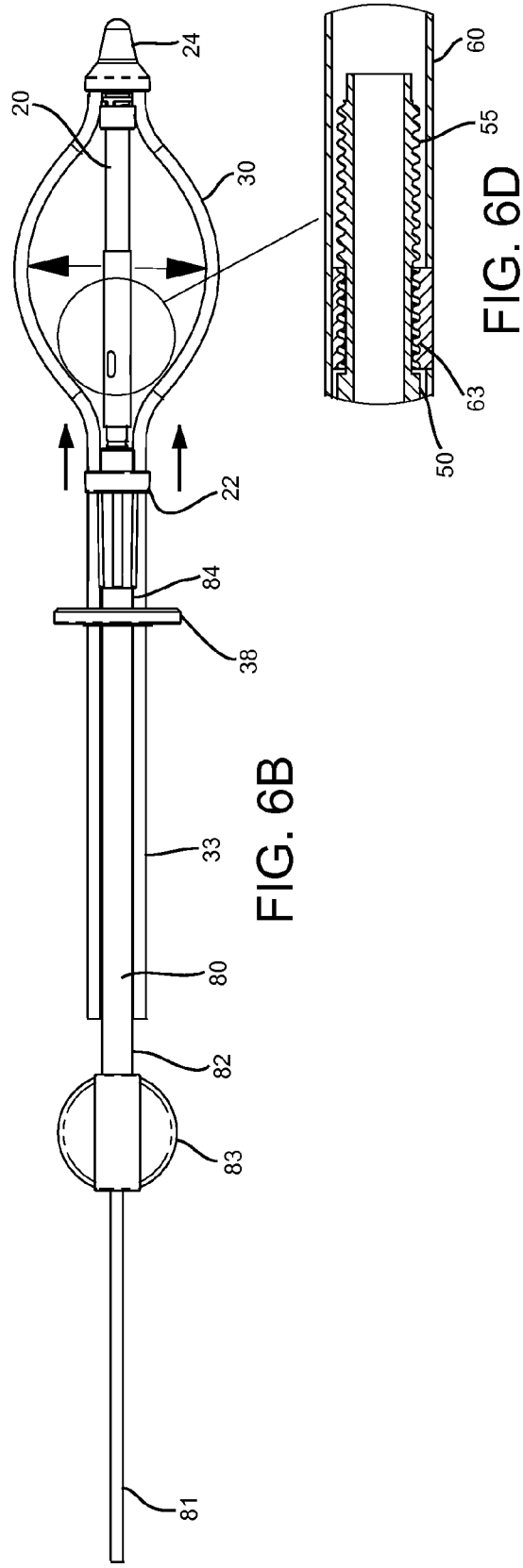

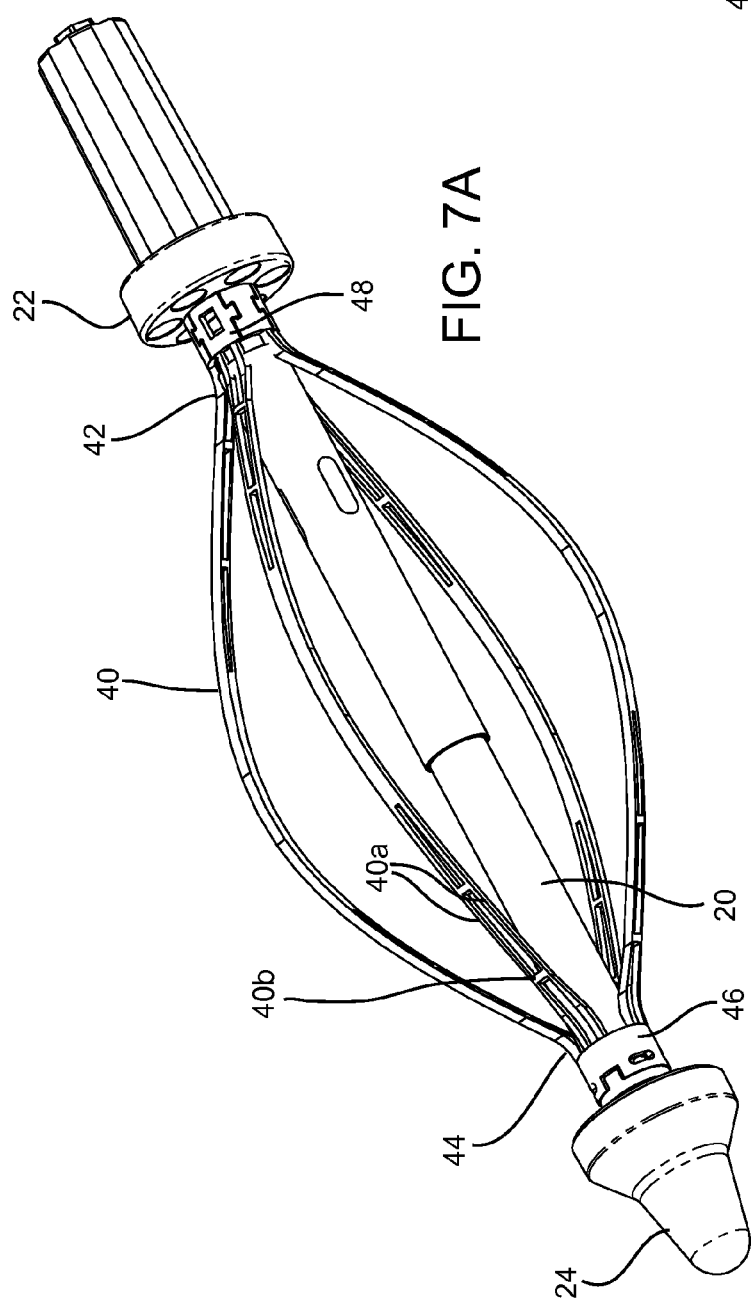
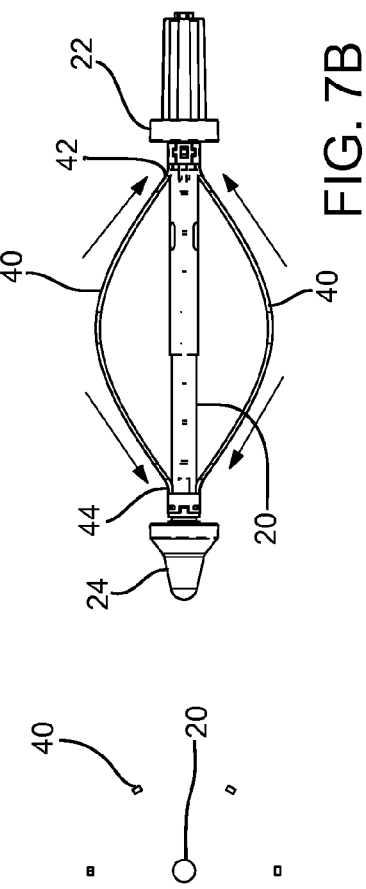
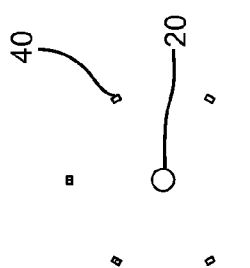
FIG. 7A
FIG. 7B
FIG. 7C

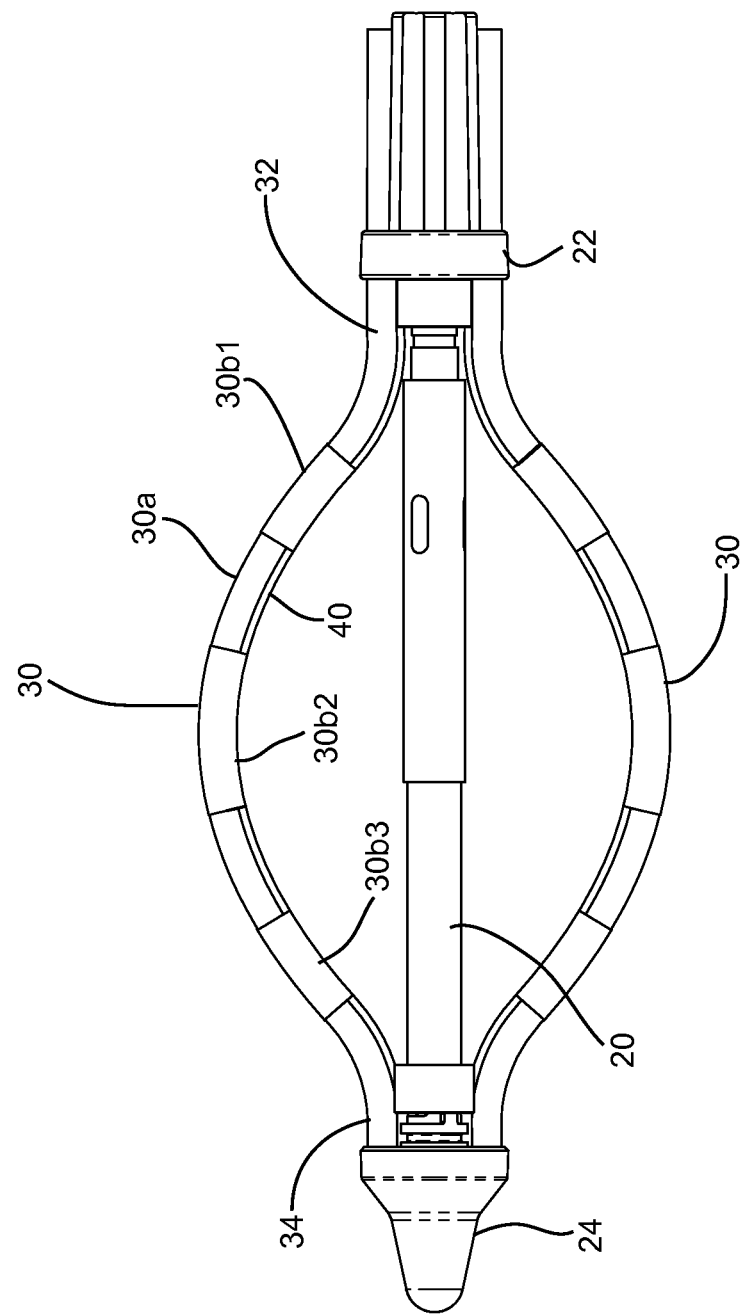

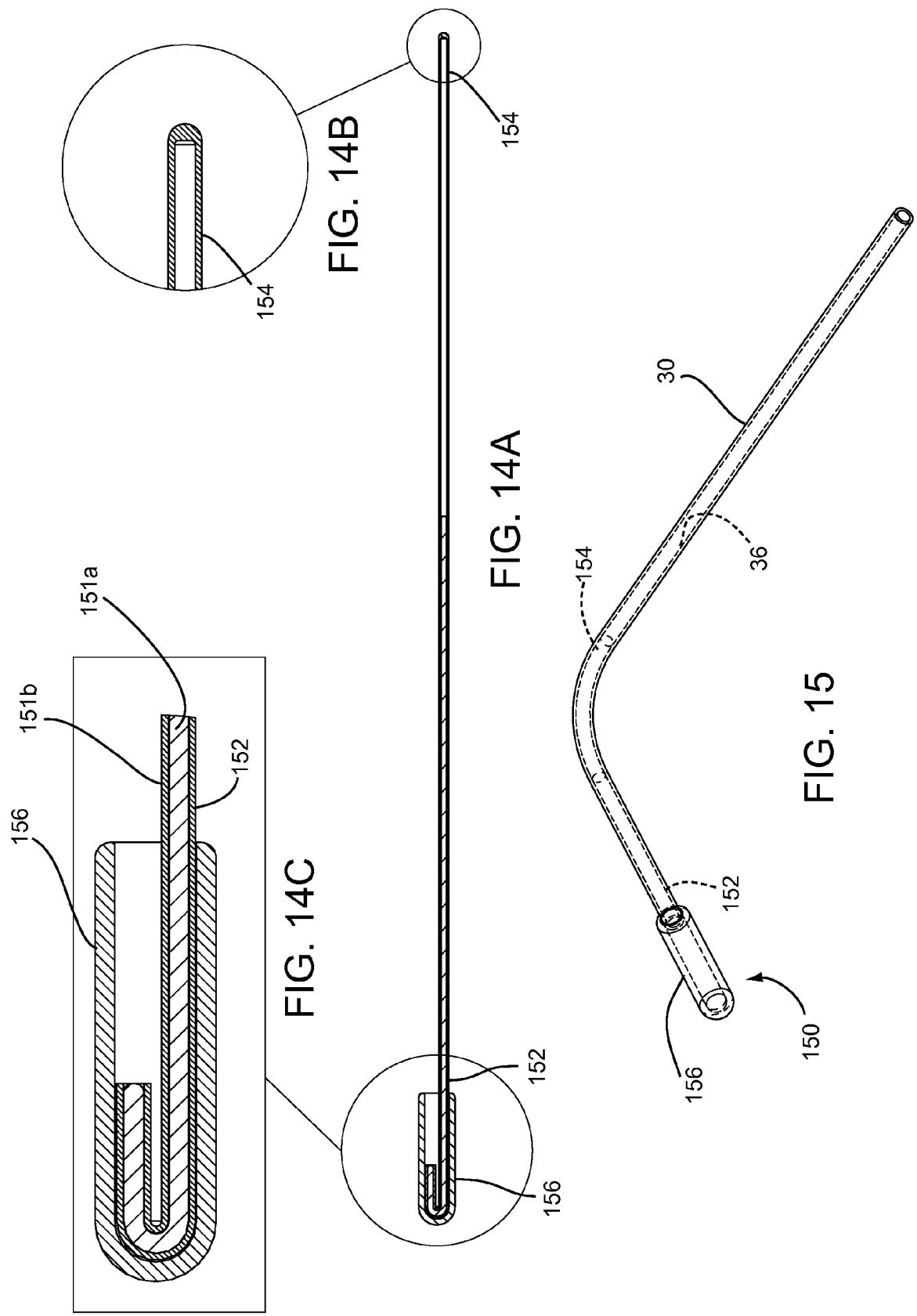

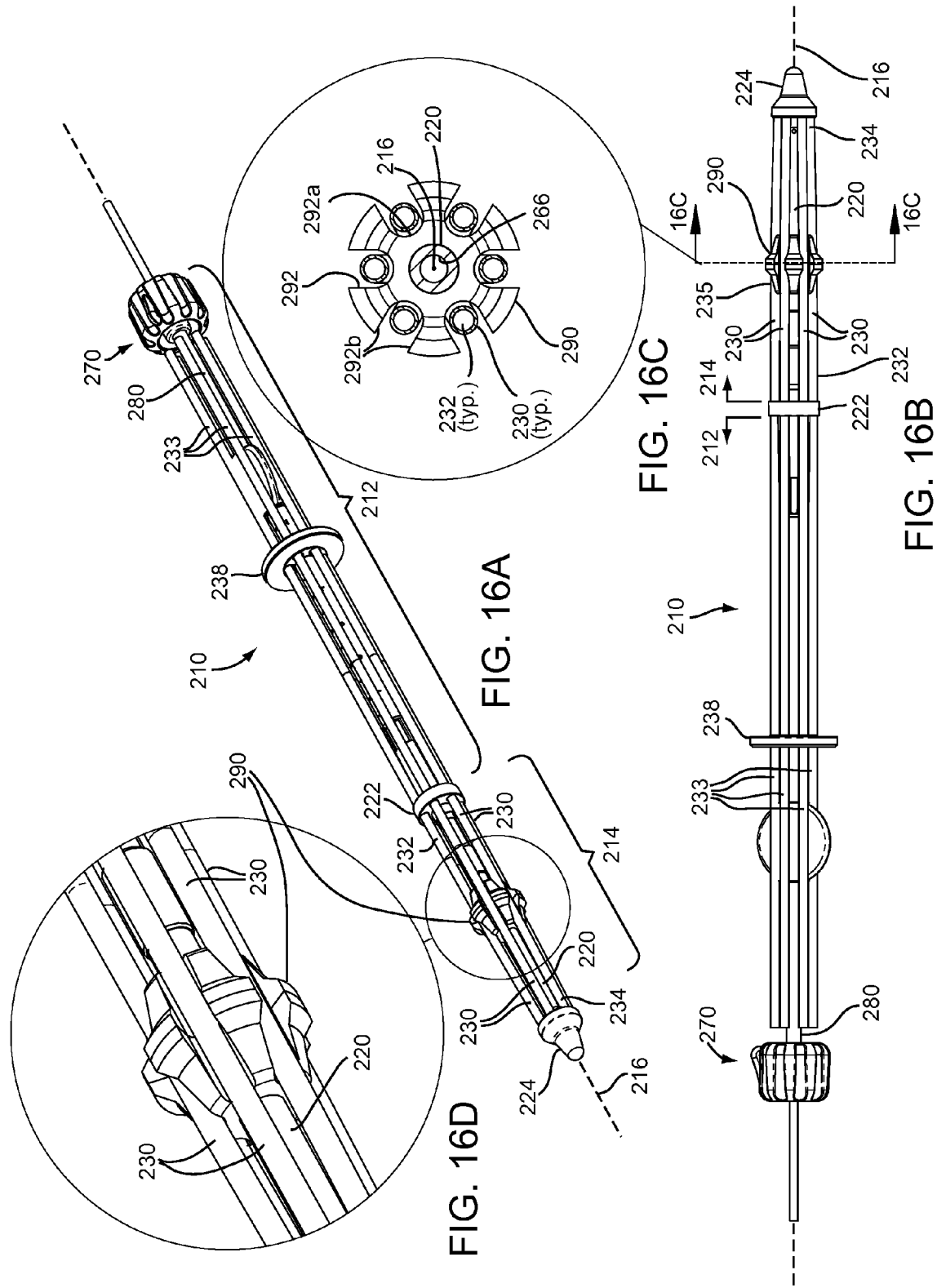

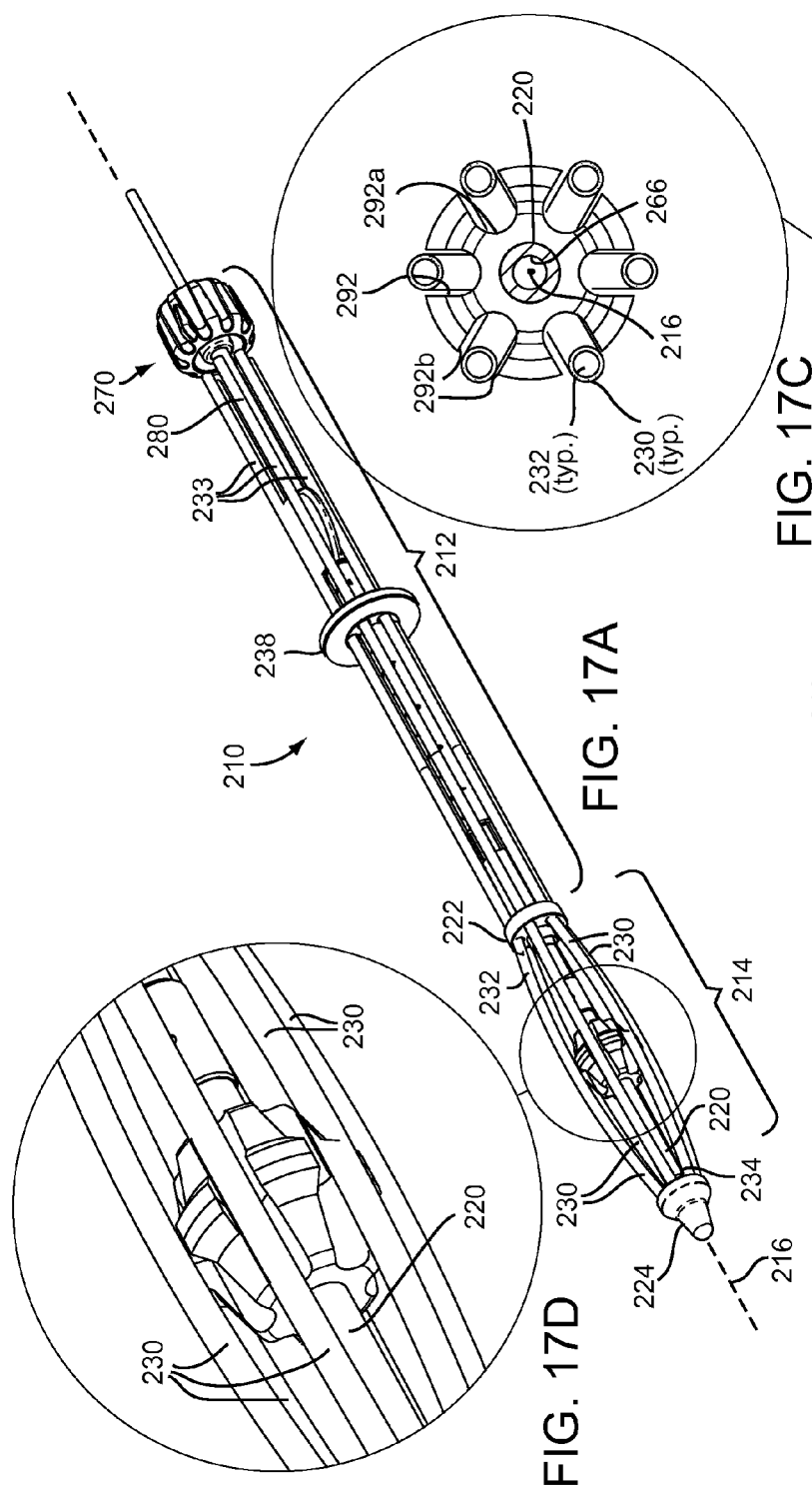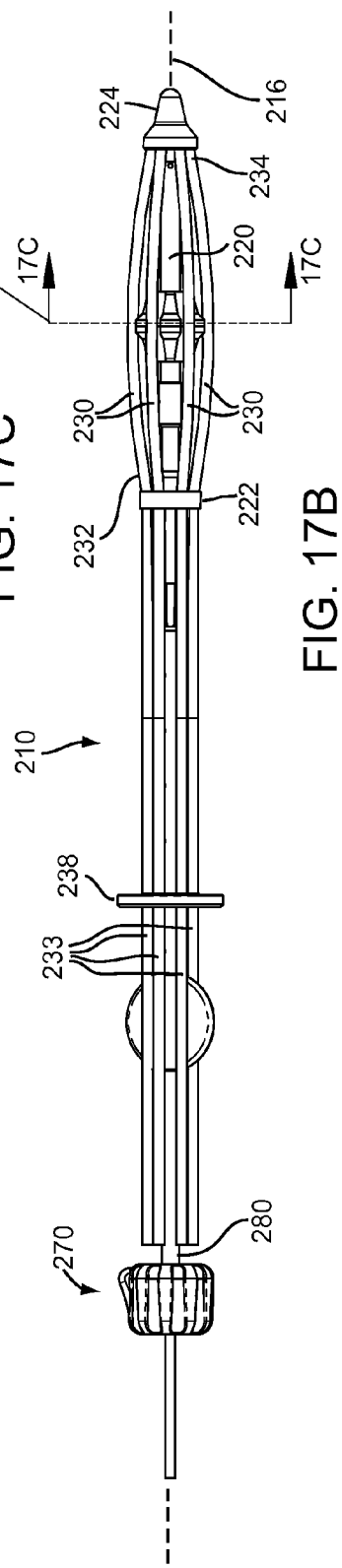

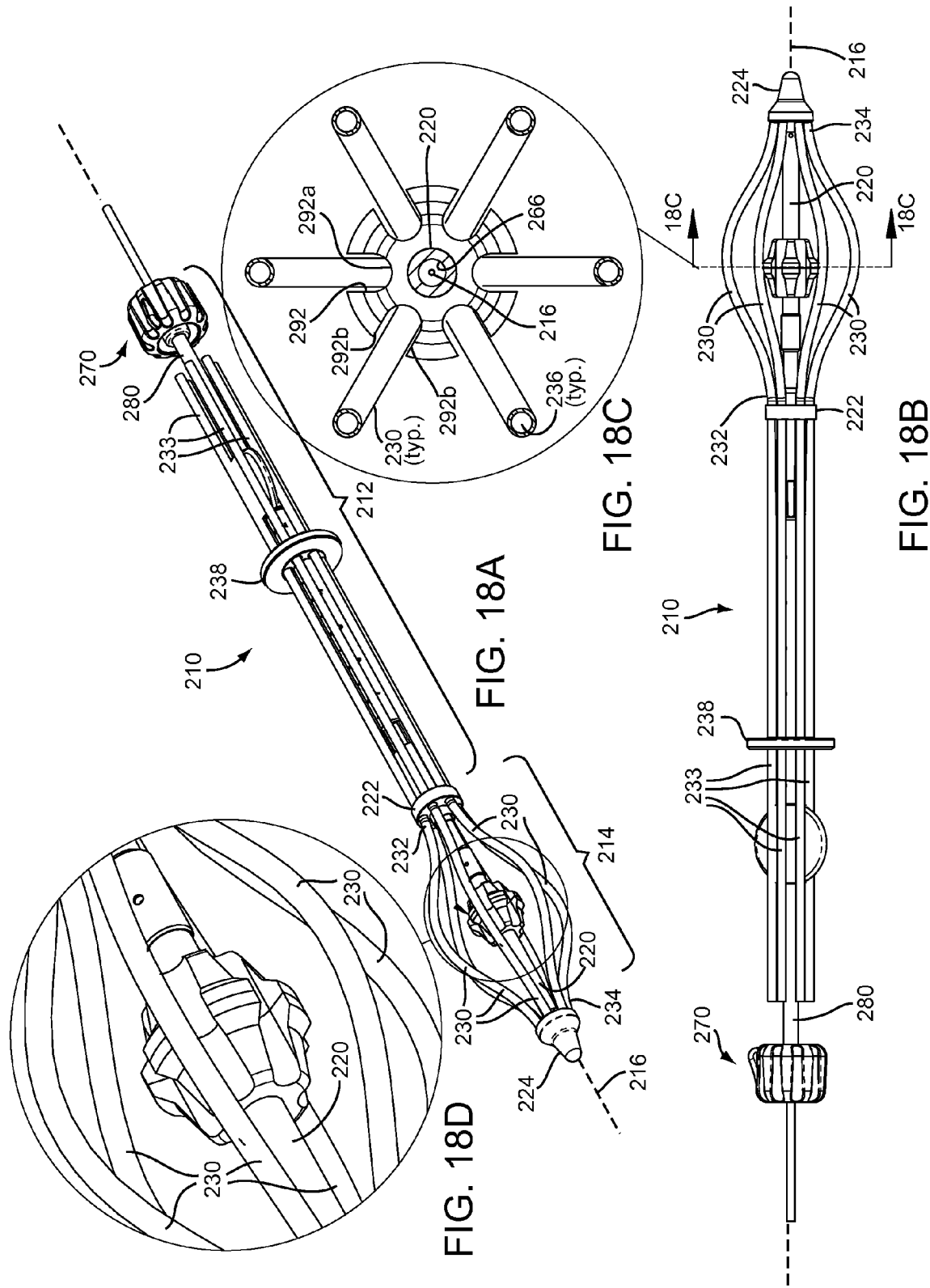

EXPANDABLE BRACHYTHERAPY APPARATUS AND METHODS FOR USING THEM

RELATED APPLICATION DATA

This application is related to applications Ser. No. 10/658,518, filed Sep. 9, 2003, 60/731,879, filed Oct. 31, 2005, 60/735,649, filed Nov. 10, 2005, 60/735,532, filed Nov. 10, 2005, 60/803,828, filed Jun. 2, 2006, Ser. No. 11/276,851, filed Mar. 16, 2006, 60/828,655, filed Oct. 8, 2006, and 61/089,855, filed Aug. 18, 2008. The entire disclosures of these applications are expressly incorporated by reference herein.

FIELD OF THE INVENTION

The present invention relates generally to apparatus, systems, and methods for providing brachytherapy to a human or other mammalian body, and more particularly to expandable apparatus for performing brachytherapy treatment within tissue, e.g., within breast tissue and/or within a body cavity, and to methods for performing brachytherapy using such apparatus.

BACKGROUND

Brachytherapy is a type of radiation therapy used to treat malignant tumors, such as cancer of the breast or prostate. In general, brachytherapy involves positioning a radiation source directly into target tissue, which may include a tumor and/or tissue surrounding a cavity or void, which may contain potentially cancerous cells (such as a cavity or void created by removing a tumor).

Brachytherapy is often divided into two categories: high dose rate (HDR) and low dose rate (LDR) brachytherapy. In HDR brachytherapy, a high activity radiation source is placed into target tissue, often via a previously implanted catheter, for a short period of time, e.g., lasting from several seconds to a few minutes. In contrast, LDR brachytherapy involves placing a low activity radiation source into the target tissue for a longer, sometimes indefinite, period of time.

Both forms of brachytherapy have advantages. For instance, HDR brachytherapy provides higher radiation levels delivered over a shorter dose delivery period. LDR brachytherapy, on the other hand, utilizes lower activity radiation sources. The energy field of the LDR radiation source results in a measured and localized dose of radiation delivered to target tissue, e.g., a tumor, gland, or other tissue surrounding a cavity or void. However, the energy field thereafter decays to avoid excessive exposure of nearby healthy tissue.

Due in part to the lower activity of LDR radiation sources, LDR brachytherapy may provide various advantages. For example, for healthcare workers, exposure precautions for LDR brachytherapy may be less stringent than those for HDR brachytherapy. Also, there are radiobiological advantages of LDR brachytherapy over HDR brachytherapy (e.g., the dose rate effect), which may lead to better sparing of normal tissue during treatment. Moreover, for patients, the relatively longer implantation period associated with LDR brachytherapy may result in fewer visits to a healthcare facility over the course of radiation treatment, as compared to HDR brachytherapy where patients must return to the healthcare facility for each fraction of radiation delivered, which, for breast brachytherapy, may typically include eight to ten (8-10) fractions.

Common radiation sources used in LDR brachytherapy include radioactive isotopes such as Palladium (Pd)-103, Iodine (I)-125, Gold (Au)-198, and Iridium (Ir)-192. While the size and shape of the isotopes may vary, they may be provided in a standardized size of cylindrically shaped capsules that are approximately the size of a grain of rice, e.g., about 0.8 millimeter in diameter and about 4.5 millimeters in length, and are often referred to as "seeds."

LDR seeds are often delivered through needles using a guide template. The guide template may include a matrix of holes that guide the longitudinal advancement of the needles to ensure their proper position relative to the target tissue. Once the needles are properly located in the target tissue, the seeds may be deposited along the longitudinal axis of each needle, after which the needles may be withdrawn.

While effective, current brachytherapy implementations have potential drawbacks. For example, LDR seeds are typically left indwelling and free floating within the target tissue and are, therefore, susceptible to migration. Moreover, once implanted, LDR seeds are generally not considered removable or repositionable. LDR brachytherapy may also require careful dose distribution calculations and seed mapping before, and often during, seed implantation. Such calculation and mapping may allow effective radiation delivery to the target tissue volume, while minimizing radiation to surrounding healthy tissue (e.g., the urethra and rectum, for example, in prostate brachytherapy). Yet, while such dose calculation and seed mapping techniques are effective, problems may exist, such as potentially significant variability in accuracy of seed placement among different clinicians.

Yet another issue with conventional LDR brachytherapy techniques is that they may require the radioactive seeds to be manipulated individually at the time of implantation, which may be a time-consuming process. Moreover, conventional LDR delivery needles are generally limited to delivering the seeds linearly (along a relatively straight line). Thus, to achieve a desired therapy profile, numerous implants (e.g., including about 50-100 seeds, as are common with prostate brachytherapy) are often required, in conjunction with potentially complex dose distribution and mapping techniques and equipment.

SUMMARY

The present invention is generally directed to apparatus, systems, and methods for delivering brachytherapy to a localized target tissue region. While potentially useful in treating most any area of the body, an exemplary application is treating breast tissue, e.g., breast tumors or lumpectomy cavities. For example, the apparatus may be used to place and remove a localized radiation source for both neoadjuvant and post-excisional treatment.

In accordance with one embodiment, a system is provided for delivering one or more therapeutic elements (e.g., radiation sources) relative to a target tissue region. Once delivered, the radiation sources may be either immediately withdrawn (e.g., in HDR applications), or left in place, e.g., implanted, for a defined period of time (e.g., in LDR applications). In either instance, the radiation sources may deliver therapy to the target tissue region in accordance with a predefined therapy profile.

In some embodiments, LDR radiation sources may be implanted and secured to the body or target tissue in such a way as to prevent or substantially limit movement of the sources relative to the target tissue. For example, the apparatus and methods described herein may facilitate indwelling therapy using pre-arranged packages of radioactive sources, e.g., seeds, but also allow easy removal of the radiation sources upon completing brachytherapy treatment.

As used herein, "radiation source" and "radioactive source" may include any therapeutic element operable to deliver a dose of radiation. For example, the radiation source may be one or more radioactive seeds or, alternatively, one or more LDR or HDR wire elements (e.g., Iridium wire), e.g., as disclosed in the applications incorporated by reference elsewhere herein.

The term "implantable," as used herein, indicates the capability of a device to be inserted into the body and then maintained in a relatively fixed or static position within the surrounding tissue for an extended period of time, e.g., an hour or more and/or several hours or more, including several days or more.

Furthermore, "target tissue," "target tissue region," "target region," and "target tissue volume," as used herein, may include any portion of a human (or other mammalian) body that has been identified to benefit from radiation therapy. For example, the target tissue region may be a tumor or lesion itself, tissue proximate or surrounding the tumor, or a cavity region created by tumor excision (such as the surrounding tissue or cavity associated with a lumpectomy cavity of the breast).

It should be noted that the apparatus, systems, and methods described herein may be used for LDR or HDR brachytherapy, as described elsewhere herein and in the applications incorporated by reference herein. Moreover, while described herein with respect to brachytherapy, the apparatus, systems, and methods may apply to other therapy regimens that benefit from the removable implantation of therapy-delivering elements. In an exemplary application, the apparatus, systems, and methods are described herein for treating breast cancer. However, it will be appreciated that the apparatus, systems, and methods described herein may be used for treating other cancers or conditions that may benefit from brachytherapy treatment.

In accordance with one embodiment, a brachytherapy treatment apparatus is provided that includes an elongate body including a proximal end and a distal end sized for introduction into a tract through tissue. A plurality of elongate members may be provided on the distal end including pathways for receiving a source of radiation therealong, the elongate members being movable from a collapsed configuration for introduction through a tissue tract to a target location, and an expanded configuration. A source of radiation may be introduceable along the pathways for delivering radiation to the target location.

In accordance with another embodiment, a method is provided for brachytherapy treatment of tissue within a body that includes creating a tract through tissue to a target location comprising a cavity, and advancing an elongate body carrying a plurality of elongate members through the tract into the target location with the elongate members in a collapsed configuration. The elongate members may be directed to an expanded configuration at the target location to position the elongate members away from a central axis such that tissue in the target region (e.g., surrounding the cavity) extends between at least a portion of adjacent elongate members, and radiation may be delivered to the target location to treat tissue at the target location.

In accordance with still another embodiment, a system for brachytherapy treatment of tissue adjacent a cavity within a body is provided that includes an expandable brachytherapy apparatus and a prep catheter including a proximal end, a distal end sized for introduction through a tissue tract into a body cavity, and an expandable member on the distal end for dilating tissue surrounding the body cavity before introducing the apparatus therein.

In accordance with yet another embodiment, a method for brachytherapy treatment of tissue is provided that includes creating a tract through tissue to a target location adjacent to a cavity; introducing a distal end of a prep catheter through the tract into the cavity;

expanding an expandable member on the distal end of the prep catheter within the cavity; and removing the prep catheter.

Thereafter, a brachytherapy apparatus may be introduced through the tract into the dilated cavity for delivering radiation. In one embodiment, elongate members on the brachytherapy apparatus may be directed to an expanded configuration at the target location to position the elongate members away from a central axis; and radiation may be delivered to the target location to treat tissue at the target location.

In accordance with still another embodiment, a system for brachytherapy treatment of tissue adjacent a cavity within a body is provided that includes a brachytherapy apparatus and an introducer sheath including a proximal end, a distal end sized for introduction through a tissue tract into a body cavity, and defining a lumen therebetween sized for receiving the apparatus therein in the collapsed configuration. The sheath may include a slit extending at least partially between the proximal and distal ends to facilitate removal of the sheath from around the apparatus after introducing the apparatus through the sheath into the body cavity.

In accordance with yet another embodiment, a method for brachytherapy treatment of tissue is provided that includes creating a tract through tissue to a target location adjacent to a cavity; introducing a distal end of an introducer sheath through the tract into the cavity; advancing a brachytherapy apparatus through the sheath; and removing the sheath from around the brachytherapy apparatus.

In accordance with still another embodiment, an apparatus for brachytherapy treatment of tissue is provided that includes an introducer sheath and a trocar removably disposed within the sheath. In one embodiment, the sheath includes a proximal end, a distal end sized for introduction through a tissue tract into a body cavity, and a lumen extending therebetween sized for receiving a brachytherapy apparatus therein. The sheath may include a slit extending at least partially between the proximal and distal ends to facilitate removal of the sheath from around a radiation apparatus introduced into the lumen of the sheath.

In accordance with yet another embodiment, a brachytherapy treatment apparatus is provided that includes an elongate body including a proximal end and a distal end configured for introduction into a tract through tissue; a plurality of elongate members on the distal end comprising pathways for receiving a source of radiation therealong, the elongate members being movable from a collapsed configuration for introduction through a tissue tract to a target location, and an expanded configuration; and a plurality of inserts including proximal ends and distal ends removably receivable along the pathways of respective elongate members. The inserts may include malleable material allowing the inserts to be bent to bend and maintain proximal ends of the elongate members in a desired shape. In addition or alternatively, the inserts may include on the proximal ends of the inserts for engaging proximal ends of the elongate members when the inserts are received within the lumens to substantially seal the lumens.

In accordance with still another embodiment, a method is provided for brachytherapy treatment of tissue within a patient's body that includes creating a tract through tissue to a target location adjacent to a cavity; advancing an elongate body carrying a plurality of elongate members through the tract into the target location with the elongate members in a collapsed configuration; introducing inserts into the elongate members; and bending portions of the elongate members that extend from the patient's body, the inserts being malleably bent to hold the portions of the elongate members in a desired shape. For example, the portions of the elongate members may be bent to place the portions adjacent the patient's skin between radiation treatments.

In accordance with yet another embodiment, a brachytherapy treatment apparatus is provided that includes an elongate core member comprising a proximal end and a distal end and defining a longitudinal axis between the proximal and distal ends, a guide member on the core member disposed between the proximal and distal ends, a distal hub coupled to the distal end of the core member, a proximal hub on the proximal end of the core member, at least one of the proximal hub and the distal hub movable axially relative to the other of the proximal hub and the distal hub, and a plurality of elongate members coupled to the proximal and distal hubs. The elongate members may include pathways for receiving a source of radiation therealong. The elongate members may be movable between a collapsed configuration wherein intermediate regions of the elongate members contact the guide member for introduction through a tissue tract to a target location, and an expanded configuration, the intermediate regions moving radially outwardly as the elongate members are directed towards the expanded configuration.

In one embodiment, the elongate members may be received in recesses in the guide member in the collapsed configuration. In addition or alternatively, the elongate members may contact the guide member such that the elongate members do not extend substantially parallel to the longitudinal axis in the collapsed configuration. For example, the elongate members may be received in recesses in the guide member in the collapsed configuration such that the elongate members are arched in the collapsed configuration. Optionally, the recesses may include side walls, e.g., that prevent substantial lateral motion of the catheters while the intermediate regions are received in the recesses.

In accordance with still another embodiment, a method is provided for brachytherapy treatment of tissue within a body, e.g., where a tract extends through tissue to a target location adjacent to a cavity. A distal portion of an elongate body may be advanced through the tract into the target location with the distal portion in a collapsed configuration. The distal portion may include a plurality of elongate members disposed around an elongate core member with intermediate regions of the elongate members contacting a guide member on the core member in the collapsed configuration. For example, the elongate members may be received in respective recesses in the guide member or may simply contact an outer surface of the guide member. The recesses may prevent substantial lateral movement of the elongate members, e.g., during initial expansion.

The distal portion may be directed to an expanded configuration at the target location wherein the elongate members expand away from a central axis and the guide member, and radiation may be delivered to the target location via the distal portion to treat tissue at the target location. In one embodiment, the elongate members may be arched in the collapsed configuration and may arch further in the expanded configuration. Such arching may resist substantial lateral movement of the elongate members, e.g., during initial expansion.

The above summary is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

FIGS. 1A and 1B are perspective views of an exemplary embodiment of a brachytherapy apparatus including an expandable therapy delivery portion in collapsed and expanded configurations, respectively.

FIG. 2A is a cross-sectional side view of the apparatus of FIGS. 1A and 1B.

FIG. 2B is a detail of a distal tip of the apparatus of FIG. 2A.

FIG. 2C is a detail of an internal actuation mechanism within the apparatus of FIG. 2A.

FIG. 3A is another cross-sectional side view of the apparatus of FIGS. 1A and 1B.

FIGS. 3B-3D are details of the apparatus of FIG. 3A, showing break-away locations to provide a bail-out mechanism for the apparatus.

FIGS. 3E and 3F are details of the apparatus of FIGS. 1A and 1B, showing an actuation mechanism within the apparatus that provides audible feedback to a user when the apparatus is expanded.

FIGS. 3G and 3H are details of a proximal end of the apparatus of FIGS. 1A and 1B, showing markers on a central catheter that provide visual feedback to a user when the apparatus is expanded.

FIGS. 5A and 5B are side views of the apparatus of FIGS. 1A and 1B, respectively.

FIG. 5C is a cross-sectional view of the apparatus of FIG. 5B, taken along line 5C-5C.

FIGS. 6A and 6B are side views of a variation of the apparatus of FIGS. 1A and 1B, respectively.

FIGS. 6C and 6D are details of the apparatus of FIGS. 6A and 6B, showing internal threads within the apparatus for expanding and collapsing the apparatus.

FIG. 7A is a perspective view of an array of expanded struts and hubs that may be provided on a therapy delivery portion of a brachytherapy apparatus, such as that shown in FIGS. 1A and 1B.

FIG. 7B is a side view of the struts and hubs of FIG. 7A.

FIG. 7C is a cross-section of the struts of FIG. 7A and 7B, taken along line 7C-7C.

FIG. 10B is a perspective view of still another embodiment of an expandable therapy delivery portion of a brachytherapy apparatus including multiple lengths of heat shrink tubing around catheter tubes and struts configured to achieve a desired radius of curvature of the catheter tubes when the apparatus is expanded.

FIG. 14A is a cross-sectional side view of a catheter protector insert that may be introduced into an individual catheter of a brachytherapy apparatus.

FIGS. 14B and 14C are details of the catheter protector insert of FIG. 14A.

FIG. 15 is a perspective view of a catheter of a brachytherapy apparatus having the catheter protector insert of FIG. 14A received therein.

FIG. 16A is a perspective view of another exemplary embodiment of a brachytherapy apparatus including an expandable therapy delivery portion in a collapsed configuration.

FIG. 16B is a side view of the apparatus of FIG. 16A.

FIG. 16C is a cross-section of the apparatus of FIGS. 16A and 16B taken along line 16C-16C of FIG. 16B.

FIG. 16D is a detail of a catheter guide of the apparatus of FIG. 16A.

FIG. 17A is a perspective view of the brachytherapy apparatus of FIG. 16A, showing the expandable therapy delivery portion in a partially expanded configuration.

FIG. 17B is a side view of the apparatus of FIG. 17A.

FIG. 17C is a cross-section of the apparatus of FIGS. 17A and 17B taken along line 17C-17C of FIG. 17B.

FIG. 17D is a detail of the catheter guide of the apparatus of FIG. 17A.

FIG. 18A is a perspective view of the brachytherapy apparatus of FIGS. 16A and 17A, showing the expandable therapy delivery portion in a fully expanded configuration.

FIG. 18B is a side view of the apparatus of FIG. 18A.

FIG. 18C is a cross-section of the apparatus of FIGS. 18A and 18B taken along line 18C-18C of FIG. 18B.

FIG. 18D is a detail of the catheter guide of the apparatus of FIG. 18A.

DETAILED DESCRIPTION OF EXEMPLARY EMBODIMENTS

Figure 4A:
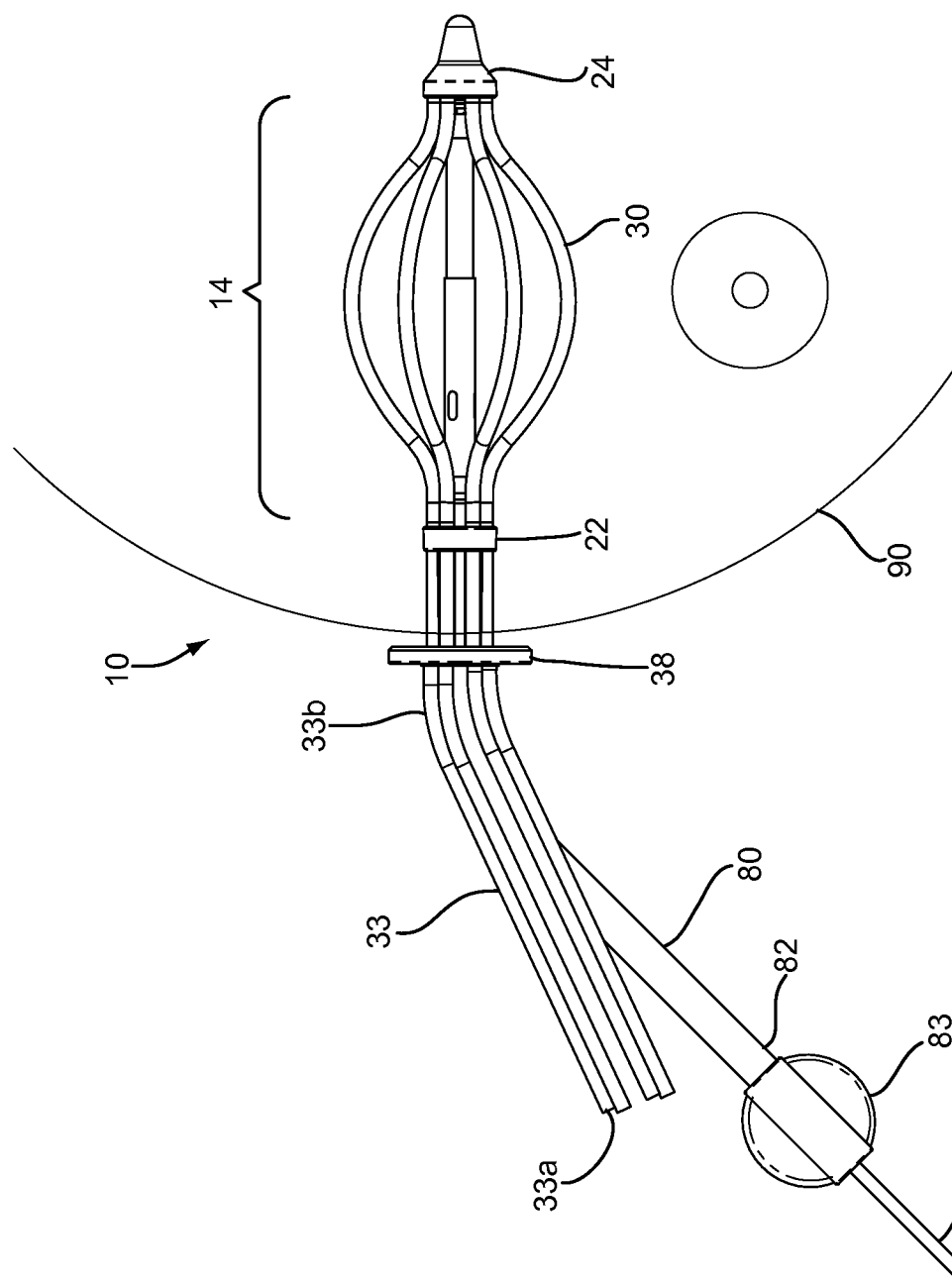
FIG. 4A is a side view of an alternative embodiment of a brachytherapy apparatus generally similar to the apparatus of FIGS. 1A and 1B, including bendable proximal regions on catheter tubes of the apparatus.

Turning to the drawings, FIGS. 1A and 1B show an exemplary embodiment of an expandable brachytherapy apparatus 10 that includes a proximal or tail portion 12, and a distal or therapy delivery portion 14, generally defining a longitudinal axis 16 extending therebetween. As described elsewhere herein, the distal portion 14 may be deployed within a target location of a patient's body, e.g., a tumor or cavity within a breast or other body structure (not shown), and the proximal portion 12 may extend from the distal portion 14, e.g., such that the proximal portion 12 protrudes at least partially outside of the body structure. The distal portion 14 may be movable between a collapsed configuration, as shown in FIG. 1A, e.g., for introduction through a tissue tract to a target location, and a fully deployed or expanded configuration, as shown in FIGS. 1B and 2A, e.g., for providing a three dimensional array of pathways at the target location, as described further below.

In addition, as shown in FIGS. 1A and 1B, the apparatus 10 may include an expansion tool 70, which may be coupled to the apparatus 10 for expanding and/or collapsing the distal portion 14, as described further below. The expansion tool 70 may be detachable from the apparatus 10 or may be permanently attached to the apparatus 10 (not shown). Optionally, the apparatus 10 may include one or more other components, e.g., a sheath or other cover (not shown), which may overly at least the therapy delivery portion 14, e.g., until deployment.

In addition or alternatively, the apparatus 10 may be part of a system, e.g., including a tubular delivery device, such as a catheter, cannula, trocar, obturator, and/or needle (also not shown), for introducing the apparatus 10 into a target location, e.g., as described in the applications incorporated by reference elsewhere herein. For example, such a system may include an introducer sheath 110 and/or trocar 120, such as that shown in FIG. 12 and described further below. In addition or alternatively, the apparatus 10 may include a sharpened distal tip (not shown), e.g., to facilitate advancement directly through tissue, also as disclosed in the applications incorporated by reference elsewhere herein.

With additional reference to FIGS. 2A-2C, the apparatus 10 includes an elongate core member 20 extending between a proximal hub 22 and a distal hub 24, and a plurality of flexible elongate members 30 disposed around the core member 20 and/or extending between the proximal and distal hubs 22, 24. The core member 20 may be a substantially rigid member extending between the proximal and distal hubs 22, 24 yet compressible and/or extendable axially to direct the proximal and distal hubs 22, 24 towards and/or away from one another, e.g., a telescoping member, as described further below.

The elongate members 30 may be elongate, fixed length tubular members or "catheters," each including a proximal end 32, a distal end 34, and a lumen 36 extending therebetween (shown in FIGS. 2A and 2B). The proximal ends 32 may be received in, through, and/or coupled to the proximal hub 22, e.g., as described elsewhere herein and in the applications incorporated by reference herein. Tubular extensions 33 may also be received in and/or coupled to the proximal hub 22 and/or coupled directly to the proximal ends 32 of the elongate members 30, e.g., extending proximally from the proximal hub 22 to at least partially define the proximal portion 12 of the apparatus 10. Each tubular extension 33 may include an opening 33a providing access into a respective lumen 36, e.g., through the tubular extension 33 into a respective elongate member 30, for receiving a radiation source, as described elsewhere herein.

Alternatively, the tubular extensions 33 may be formed as an integral part of the elongate members 30, e.g., as a continuous extrusion, molding, and the like, such that the elongate members 30 extend from the openings 33a to the distal ends 34.

The tubular extensions 33 may remain substantially free relative to one another or may be at least partially constrained relative to one another. For example, as shown in FIGS. 1A and 1B, a collar 38 may be provided that includes openings for receiving respective tubular extensions 33 therethrough, thereby keeping the tubular extensions 33 together, organized, and/or otherwise limit relative movement of the tubular extensions 33. The collar 38 may be fixed axially or may be movable axially relative to the tubular extensions 33.

Generally, the tubular extensions 33 may be flexible, e.g., to allow the tubular extensions to be curved or otherwise bent individually and/or together. Thus, the proximal portion 12 of the apparatus 10 may be easily bent, e.g., to accommodate securing the proximal portion 12 to a patient, for example, to the patient's skin adjacent a tract communicating with a treatment site within which the distal portion 14 has been introduced. It may be desirable for any bending of the tubular extensions 33 not to apply pressure to the distal portion 14 and/or treatment site, e.g., due to cantilever effects. For example, as shown in FIG. 4A, an apparatus 10 is shown introduced into a breast 90 that includes tubular extensions 33 including bendable regions 33b adjacent the collar 38. The bendable regions 33b, the rest of the tubular extensions 33, and/or the entire elongate members 32 may be formed from a fluoropolymer resin, thermoplastic elastomer, and the like, e.g., having a maximum durometer of 55 D. Such material may allow the bendable regions 33b (and/or other regions of the proximal portion 12) to be bent or otherwise directed laterally relative to the distal portion 14 without buckling and/or applying substantial lateral stress to the breast 90.

In addition or alternatively, the core member 20 may be coupled to a flexible shaft 80 extending proximally from the proximal hub 22 or collar 38. Thus, the shaft 80 and the tubular extensions 33 may substantially define the proximal portion 12 of the apparatus 10.

Generally, the shaft 80 may include a proximal end 82, a distal end 84 coupled to the proximal hub 22, and a lumen 86 extending therebetween. Thus, the shaft 80 may be coupled such that any axial movement of the proximal hub 22 causes corresponding axial movement of the shaft 80. The lumen 86 may be sized to receive the expansion tool 70, as explained further below. In addition or alternatively, the lumen 86 may be sized to receive a central catheter tube 81, which may extend through the lumen 86, into the core member 20, and optionally into the distal hub 24. The shaft 80 may be formed from flexible material that may provide sufficient flexibility and torque resistance, thereby also minimizing stress on the breast 90. For example, the shaft 80 may be formed from stainless steel or other braided tubing, which may accommodate bending of the shaft 80 along with the tubular extensions 33.

Figure 4B:
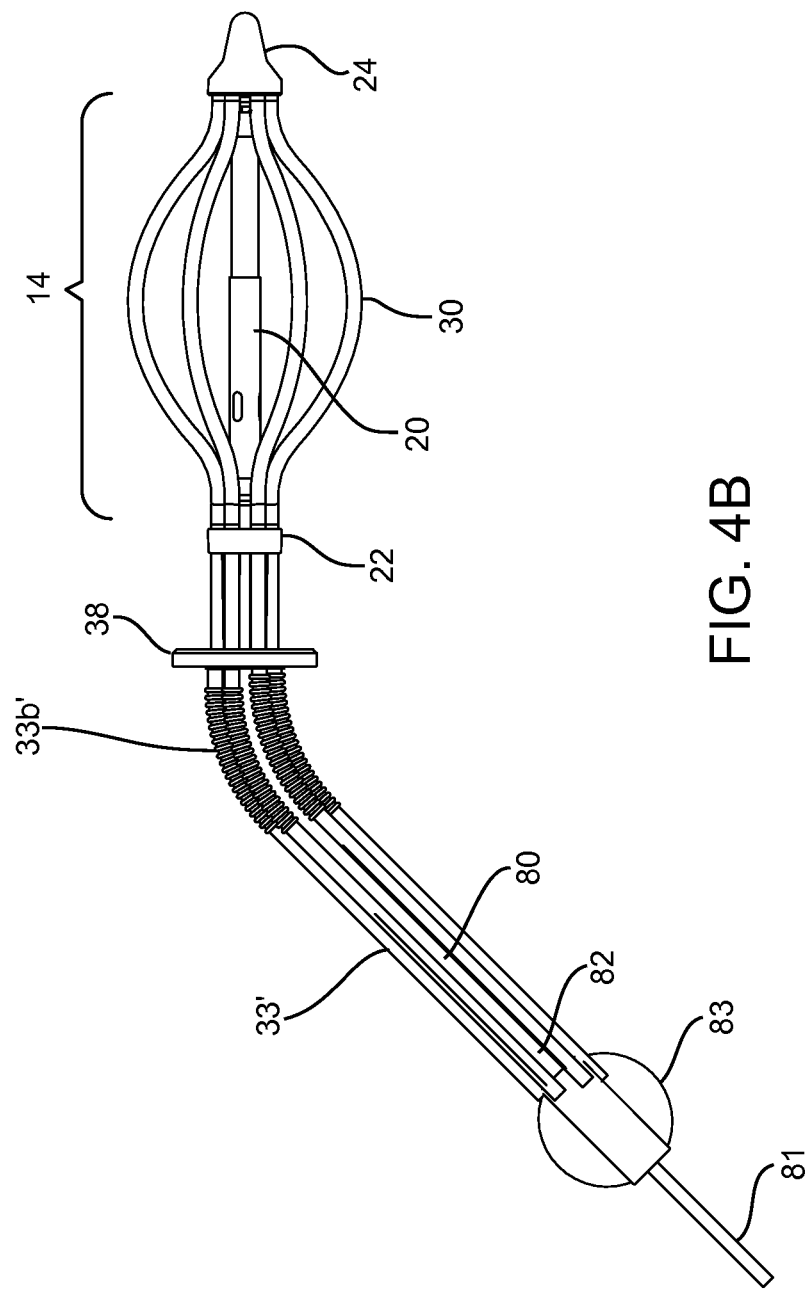
FIG. 4B is a side view of another alternative embodiment of a brachytherapy apparatus, including bendable proximal regions on catheter tubes of the apparatus.
Figure 4C:
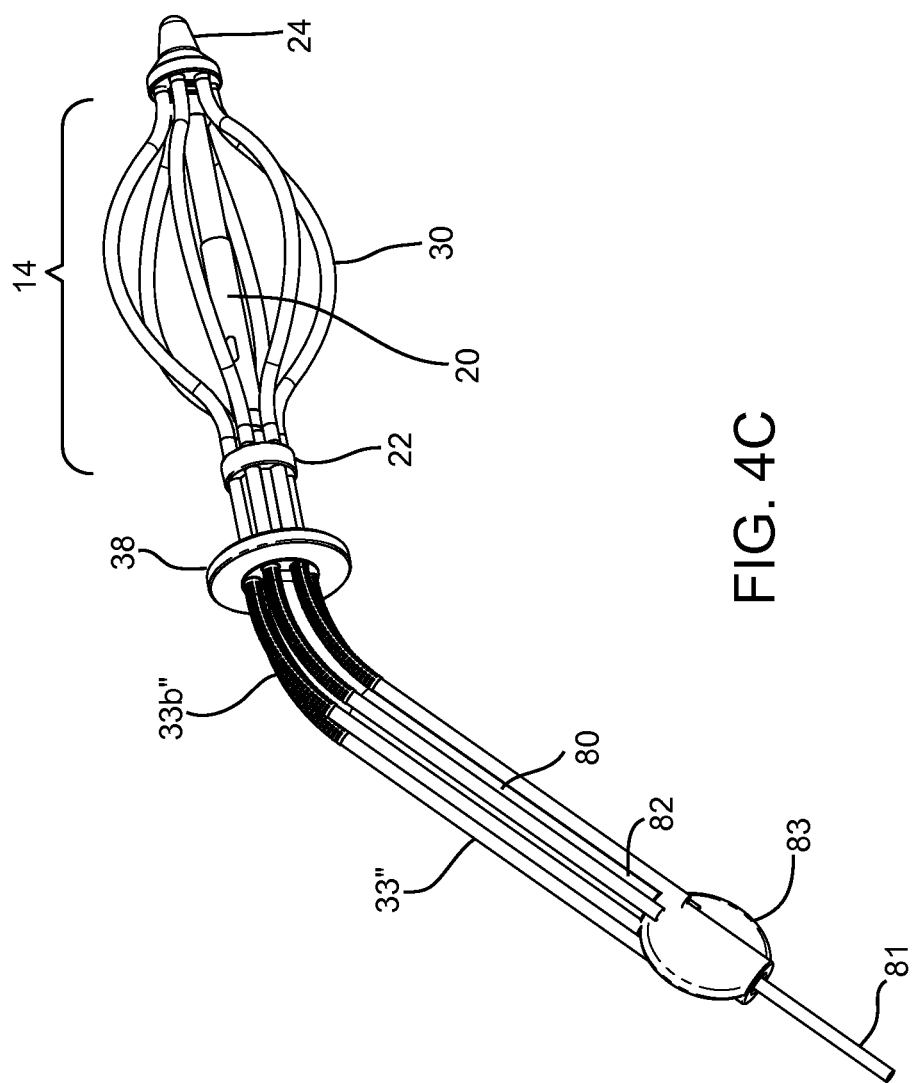
FIG. 4C is a perspective view of yet another alternative embodiment of a brachytherapy apparatus, including bendable proximal regions on catheter tubes of the apparatus.

Optionally, the tubular extensions (or the elongate members themselves if provided as one continuous tubular member) may include one or more features to facilitate bending and/or conformability of the proximal portion 12 of the apparatus 10. For example, as shown in FIG. 4B, tubular extensions 33' may include corrugated regions 33b' that may allow bending without substantial risk of kinking. The corrugated regions 33b' may maintain any shape to which they are bent, e.g., substantially maintaining a desired shape without applying stress to other regions of the apparatus 10, to the access site, and/or otherwise to the patient's body. Alternatively, as shown in FIG. 4C, tubular extensions 33" may be provided that include bendable regions 33b" made from reinforced or composite tubing. The tubing may include one or more reinforcement elements, e.g., a braid, thin metal strips, and the like (not shown), that allow bending without substantial risk of kinking the tubing. The bendable regions 33b" may be malleable such that the tubular extensions 33 may be bent into any desired curved shape, yet may be returned to a straightened (or other) shape, as desired during use. Optionally, the entire tubular extensions may be formed from such bendable and/or malleable material (not shown).

Figure 4D:
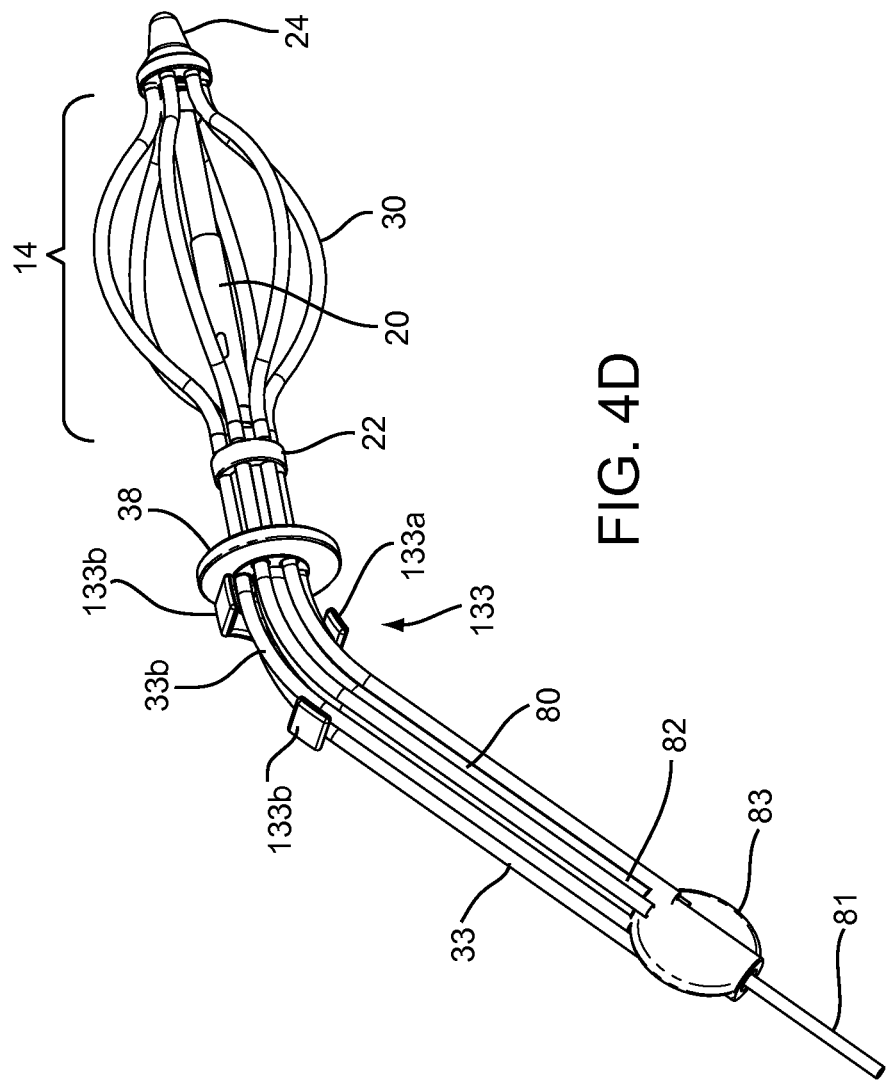
FIG. 4D is a perspective view of still another alternative embodiment of a brachytherapy apparatus, including a clamp applied on a proximal portion of the apparatus for bending the proximal portion.

In another alternative, shown in FIG. 4D, a clip, clamp, or other tool 133 may be used to cause localized bending, e.g., at the bendable regions 33b of the tubular extensions 33. The clip 133 may including opposing arms 133a, 133b that may be opened (not shown) to allow the clip 133 to be positioned around the tubular extensions 33. The opposing arms 133a, 133b may be biased to close and/or may be mechanically closed such that one arm 133a applies a transverse force between the opposing arms 133b, thereby causing the bendable regions 33b to bend locally without translating substantial force to other regions of the tubular extensions 33, and consequently to the patient and/or other regions of the apparatus 10.

In addition or alternatively, as shown in FIGS. 14 and 15, catheter protector inserts 150 may be provided, e.g., as part of an apparatus or system along with the apparatus 10 (only an individual elongate member or catheter 30 being shown in FIG. 15 for simplicity). Generally, as best seen in FIG. 14A, each catheter protector insert 150 is an elongate body including a proximal end 152 and a distal end 154 sized for introduction into a lumen 36 of a catheter 30. In addition, the insert 150 may include an end cap 156 on the proximal end 152, e.g., for sealing the lumen 36 of an elongate member 30, as described further below.

The insert 150 may have a length corresponding to the length of the elongate members 30, e.g., at least as long as the elongate member 30. Alternatively, the insert 150 may have a relatively shorter length than the elongate member 30, e.g., such that the insert 150 only extends partially into the elongate member. For example, as shown in FIG. 15, the insert 150 may be inserted into the lumen 36 of an elongate member 30 until the distal end 154 is disposed within an intermediate region of the elongate member 30, e.g., at least partially into the proximal portion 12 of an apparatus 10 (not shown). Similarly, an insert 150 (not shown) may be inserted into each elongate member 30 of the apparatus 10.

The insert 150 may be formed from a plastic-covered malleable core 151a. For example, the core 151a may be a wire, shaft, or tube of malleable material, such as fully annealed metal, e.g., Type 304 stainless steel. The core 151a may be covered with a coating 151b, e.g., a length of heat shrink tubing, a dipped coating, and the like. Optionally, the distal end 154 of the insert 150 may be covered by the plastic coating, as shown in FIG. 14B. The proximal end 152 of the insert 150 may be attached to the cap 156, e.g., by folding the proximal end 152 and substantially permanently attached to the cap 156, e.g., using an interference fit, bonding with adhesive, and the like, as shown in FIG. 14C.

Optionally, the insert 150, e.g., the core 151a, may be formed at least partially from radiopaque material and/or one or more radiopaque markers (not shown) may be provided on the insert 150, e.g., on the distal end 154, similar to the marker devices disclosed in application Ser. No. 11/868,483, filed Oct. 6, 2007, incorporated by reference herein. The radiopacity of the insert 150 may enhance monitoring the location and/or orientation of the elongate members 30 within a patient's body, e.g., using fluoroscopy or other external imaging.

During use, the distal end 154 of the insert 150 may be inserted into a catheter 30, as shown in FIG. 15. For example, the insert 150 may be advanced until the cap 156 is received over the catheter 30. Thus, the cap 156 may enhance sealing of the lumen 36 to prevent debris or other material from entering the lumen 36, e.g., between treatments of a patient. In addition, the malleable nature of the core 151a allows the insert 150 to be manipulated, e.g., to bend the catheter 30. For example, between treatments, the insert 150 may be bent to place the portion of the catheter 30 extending from the patient's body placed against the patient's skin or otherwise to maximize comfort for the patient. During a subsequent treatment, the inserts 150 may be removed, and one or more radiation sources (not shown) introduced into the catheters 30, as described further elsewhere herein.

Returning to FIGS. 1A and 1B, the elongate members 30 may be formed from a single extrusion separated to provide the set of elongate members 30, individual extrusions or other tubular bodies, or may be formed from multiple tubular bodies connected to one another, e.g., by bonding, fusing, lapping, and the like, as described in the applications incorporated by reference herein. In one embodiment, the tubular members 30 and extensions 33 may be formed from a single extrusion (not shown), and the extrusion may be at least partially slit to separate portions of the tubular members 30 and extensions 33. For example, the extrusion may be slit at least partially along the distal portion 14 between the proximal and distal hubs 22, 24 to define individual elongate members 30, and/or the proximal portion 12 may be slit from the proximal end to a location adjacent the proximal hub 22 to define the extensions 33.

In another embodiment, the elongate members 30 may include separate catheter tubes 30a coupled to struts or other supports 40, as described elsewhere herein. Alternatively, the elongate members 30 may be elongate tubular extrusions have asymmetrical cross-sections, thereby biasing the elongate members 30 to buckle and/or otherwise expand in a predetermined manner, as described elsewhere herein and in the applications incorporated by reference.

The proximal hub 22 may be provided from one or more pieces, e.g., including an annular collar 23 that includes passages for receiving the proximal ends 32 of the elongate members 30 and/or an inner main tube hub 22a that is coupled to the core member 20. The annular collar 23 and tube hub 22a may be integrally molded, machined, or otherwise formed together from a single piece. Alternatively, the proximal hub 22 may be formed from separate components that are attached together, e.g., using an interference fit, cooperating connectors, bonding using adhesive, sonic welding, and the like. Optionally, the proximal hub 22 may include features, e.g., an external collar or sleeve (not shown), for securing a portion of the elongate members 30 relative to the proximal hub 22, as described further below.

Similar to the proximal hub 22, the distal hub 24 may be formed from one or more components integrally molded, machined, or otherwise formed together from a single piece, or as separate components that are attached together. As best seen in FIG. 2B, the distal ends 34 of the elongate members 30 may be received within and/or secured to the distal hub 24. For example, the distal hub 24 may include an annular recess or individual pockets into which the distal ends 34 may be received and secured, e.g., using an interference fit, bonding with adhesive, sonic welding, mating connectors, and the like.

In addition, the distal hub 24 may include a central recess 25 communicating with and/or receiving the core member 20. The central recess 25 and/or core member 20 may extend distally beyond the distal ends 34 of the elongate members 30, e.g., at least about 0.7 centimeter beyond the distal ends 34. For example, the central catheter tube 81 may extend into the central recess 25, thereby providing a central pathway extending distally beyond the elongate members 30, e.g., for receiving a radiation source therein. This may allow delivery of radiation to a distal-most portion of a cavity or other treatment site via the central recess 25, which may provide improved homogeneity of a dose plan during treatment and/or reduce "hot spots."

The distal hub 24 may provide a rounded and/or tapered distal tip for the apparatus 10, e.g., to facilitate substantially atraumatic introduction into a patient's body. Alternatively, the distal hub 24 may include a pointed or other sharpened distal tip for facilitating advancing the apparatus 10 directly through tissue (not shown), e.g., by dissection or puncture of tissue between the patient's skin and a target location. Optionally, the distal hub 24 (and/or other components of the apparatus 10) may include radiolucent material, e.g., non-metallic material such as glass-filled nylon combined with isoprene rubber, echogenic material, and the like, to facilitate monitoring the distal hub 24 (and/or apparatus 10) using external imaging.

With additional reference to FIGS. 7A-7C, the elongate members 30 may include one or more supports 40, e.g., extending at least partially between the proximal ends 32 and the distal ends 34 (not shown, see FIGS. 1A and 1B), i.e., along at least the distal portion 14 of the apparatus 10. In an exemplary embodiment, the supports 40 may be elongate strips of material, e.g., metal, such as stainless steel or Nitinol, plastic, or composite material, that may be elastically deflected during use of the apparatus 10, e.g., when the distal portion 14 is directed between the collapsed and expanded configurations.

Generally, the supports 40 include a circumferential or transverse "width" and a radial "thickness," e.g., having a rectangular cross-section, as best seen in FIG. 7C. As shown, the width may be greater than the thickness, e.g., to cause preferential bending of the supports 40 radially outwardly with minimal circumferential or transverse movement. The supports 40 may have a substantially homogeneous cross-section along their lengths or may have varying cross-sections. For example, as shown in FIG. 7A, the supports 40 may include proximal and distal ends 42, 44 having a width greater than midpoints and/or the rest of the supports 40. Such wider proximal and distal ends 42, 44 may enhance rigidity of the supports 40 transversely while allowing bending radially outwardly. In addition or alternatively, at least portions of the supports 40 may have material removed to provide greater flexibility and/or other properties. For example, as best seen in FIG. 7A, the supports 40 may include regions having material removed to define spaced apart axial struts 40a connected together by circumferential struts 40b.

The proximal ends 42 of the struts 40 may be attached or secured to the proximal hub 22 and/or the proximal ends 32 of the elongate members 30, and the distal ends 44 may be attached or secured to distal hub 24 and/or the distal ends 34 of the elongate members 30. For example, the distal ends 44 may be integrally formed with a sleeve or collar 46 that may be received around and/or otherwise secured to the distal hub 24. The sleeve 46 may be secured to the distal hub 24 using an interference fit, mating connectors, bonding with adhesive, sonic welding, and the like.

In addition, the proximal ends 42 may include connectors 48 that may be interlocked with one another and/or the proximal hub 22. Alternatively, the proximal ends 42 may be integrally formed with a collar or sleeve (not shown), similar to the sleeve 46. For example, the connectors 48 may receive mating features on the proximal hub 22 that may be snapped into or otherwise secured to the connectors 48, and consequently secure the individual proximal ends 42 to the proximal hub 22. In addition or alternatively, the proximal hub 22 and/or distal hub 24 may include a collar (not shown), which may be snapped around or otherwise secured over the connectors 48 and/or sleeve 46 in addition to or instead of other connectors, bonding, and/or other connections described above.

In one embodiment, the supports 40, collar 46, and connectors 48 may be integrally formed as a single piece, e.g., by providing a tube having a desired size and shape corresponding to the supports 40 in the collapsed configuration. The tube may have material removed to define the individual supports 40 and/or struts 40a, 40b, the collar 46, and/or the connectors 48. Alternatively, the collar 46 and/or connectors 48 may be separate components attached to the supports 40, e.g., by bonding with adhesive, sonic welding, welding or fusing, and the like.

The collar 46 and/or connectors 48 may substantially secure the proximal and distal ends 42, 44 of the supports 40, e.g., to reduce twisting of the supports 40, transverse movement of the supports 40, migration of the supports 40, and the like. For example, the proximal hub 22 may include an annular groove, a plurality of axial grooves, and the like (not shown) and the proximal ends 42 of the supports 40 may be received within respective grooves.

The supports 40 may be oriented such that their major dimension or width is disposed generally circumferentially relative to the core member 20 and their minor dimension or thickness is disposed generally radially. In the collapsed configuration, the supports 40 may extend substantially axially, i.e., substantially parallel to the core member 20 and/or longitudinal axis 16. As described further below, when the proximal and distal hubs 22, 24 are directed towards one another, the supports 40 may bow radially outwardly between the proximal and distal ends 42, 44, thereby controlling expansion of the elongate members 30 as they are directed towards the expanded configuration.

For example, the supports 40 may bias the elongate members 30 to be spaced substantially uniformly from one another about the circumference when the apparatus 10 is expanded. In an exemplary embodiment, the maximum spacing of the supports 40, and consequently, the elongate members 30, may be not more than about 1.5 centimeters, e.g., at the midpoints of the supports 40.

The configuration of the apparatus 10 may be identified based upon an axial length "L" of the distal portion 14, as shown in FIGS. 5A and 5B, and a maximum diameter "D" of the elongate members 30, as shown in FIG. 5C. These parameters may be controlled to fit within a body cavity more efficiently. For example, multiple apparatus, similar to apparatus 10, may be provided in a kit, each apparatus including a different axial length "L" and/or maximum diameter "D" such that an appropriate apparatus may be selected from the kit based upon the specific anatomy encountered in each patient. In addition or alternatively, a ratio of L/D may be used to identify the apparatus in a kit. For example, the ratio of L/D may be between about one and two (1.0-2.0), or between about 1.0-1.7, e.g., about 1.3, 1.6, or 1.7.

During manufacturing and/or assembly, the supports 40, collar 46, and connectors 48 may be formed as described above or using other methods. The sleeve 46 may be attached to the distal hub 24, e.g., using an interference fit, one or more mating connectors, bonding with adhesive, sonic welding, and the like, while the connectors 48 may remain initially free. The supports 40 may then be disposed along an outer surface of respective tubular members 30a, e.g., along a side closest to the core member 20. The supports 40 may be attached or otherwise secured to the tubular members 30a, e.g., using shrink tubing, bonding with adhesive, sonic welding, and the like, thereby providing the elongate members 30. For example, heat shrink tubing 30b may be provided along at least a portion of the tubular members 30a between the proximal and distal ends 32, 34 of the elongate members 30.

Figure 10A:
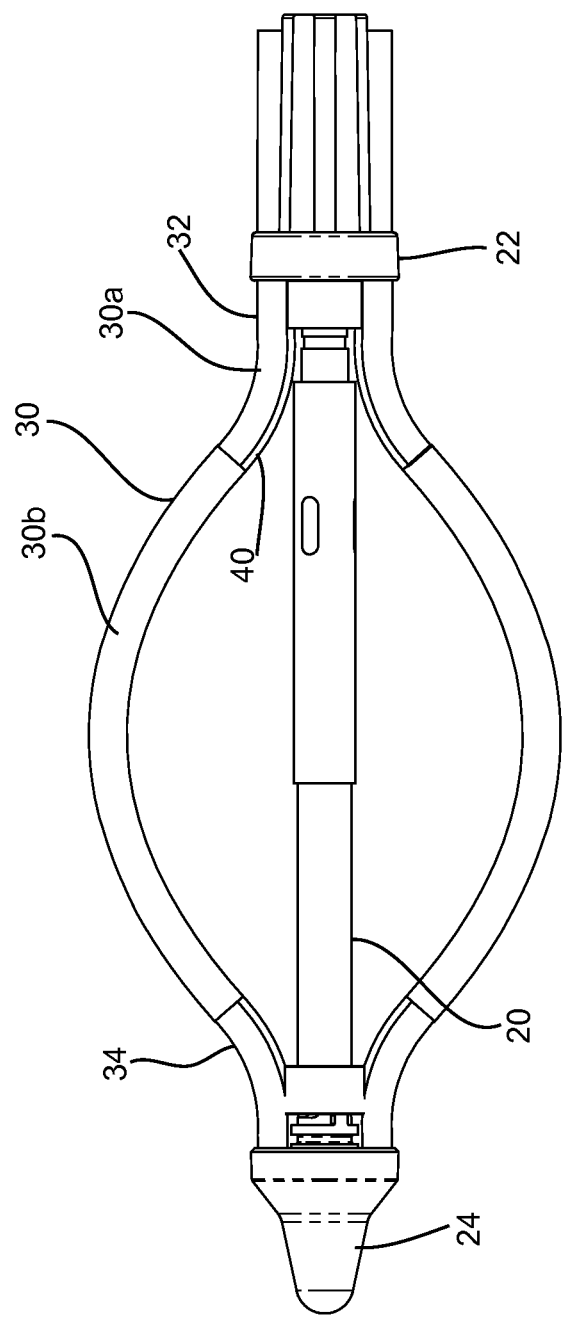
FIG. 10A is a perspective view of another embodiment of an expandable therapy delivery portion of a brachytherapy apparatus including heat shrink tubing around catheter tubes and supports to achieve a desired radius of curvature of the catheter tubes when the apparatus is expanded.

As shown in FIG. 10A, a length of heat shrink tubing 30b shorter than the tubular members 30a may be directed over the connectors 48 and around the tubular members 30a and supports 40. Heat may then be applied, e.g., hot air, to cause the heat shrink tubing 30b to shrink and capture the tubular members 30b and supports 40 therein, i.e., to secure the tubular members 30a to the supports 40. The heat shrink tubing 30b may have substantially uniform thickness and/or other properties along its length or it may be varied. The heat shrink tubing 30b may bias the elongate members 30 to a desired or maximum radius of curvature. Alternatively, multiple layers of heat shrink tubing (not shown) may be provided at one or more locations along the length of the elongate members 30.

In another alternative embodiment, shown in FIG. 10B, several relatively short sections of heat shrink tubing 30b may be provided around the tubular members 30a and supports 40. As shown, for each elongate member 30, a first section 30b1 of heat shrink tubing may be provided adjacent the proximal end 32, a second section 30b2 may be provided at a midpoint, and a third section 30b3 may be provided adjacent the distal end 34. The sections of heat shrink tubing 30b may bias the elongate members 30 to adopt a desired radius of curvature during expansion. For example, it may be desirable to have the local radius of curvature of the elongate members 30 along their lengths remain below a desired radius, e.g., not more than about 1.7 centimeters. Such a maximum radius of curvature may facilitate introducing one or more sources of radiation (not shown) into the elongate members 30. For example, some HDR radiation sources may be rated to be bent at no more than about 1.1, 1.4, or 1.7 centimeters radius of curvature.

Alternatively, the supports 40 may be provided within an additional lumen (not shown) within the elongate members 30, similar to embodiments disclosed in the applications incorporated by reference elsewhere herein. The connectors 48 may then be attached or otherwise secured to the proximal hub 22, as described elsewhere herein and/or in the applications incorporated by reference herein.

In a further alternative, the supports 40 may be eliminated. For example, the elongate members 30 may be configured, e.g., may have asymmetrical cross-sections providing a moment of inertia that biases the elongate members 30 to expand radially outwardly in a predetermined manner, as disclosed in the applications incorporated by reference herein. Optionally, the supports 40 may provide shielding, in addition to or instead of supporting the elongate members 30, also as disclosed in the applications incorporated by reference herein.

Figure 8:
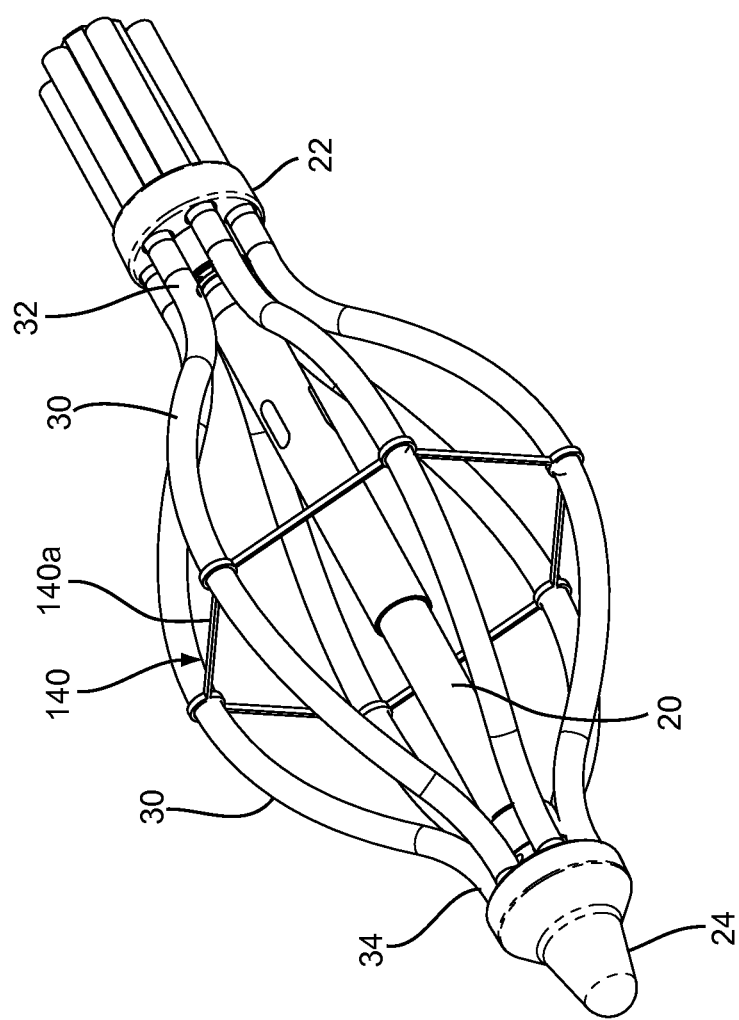
FIG. 8 is a perspective view of an alternative embodiment of an expandable therapy delivery portion of a brachytherapy apparatus including a support structure for providing a desired spacing of catheter tubes when the apparatus is expanded.

Turning to FIG. 8 in another alternative, one or more connecting members 140 may be coupled to the elongate members 40, e.g., at midpoints thereof, to provide a substantially uniform spacing of the elongate members 40 after expansion. The connecting members 140 may include a plurality of tethers 140a extending between and/or coupled to adjacent elongate members 30. The tethers 140a may be sufficiently flexible to accommodate directing the elongate members 30 inwardly, e.g., when the apparatus 10 is collapsed, yet substantially inelastic such that, upon expansion of the apparatus 10, the tethers 140a substantially maintain the circumferential spacing of the elongate members 30 relative to one another. Optionally, multiple connecting members (not shown) may be provided at various locations between the proximal and distal ends 32, 34 of the elongate members 30. Each connecting member may include tethers having different lengths corresponding to the desired spacing and overall diameter of the elongate members 30 at the axial location where the respective connecting members are provided.

Figure 9:
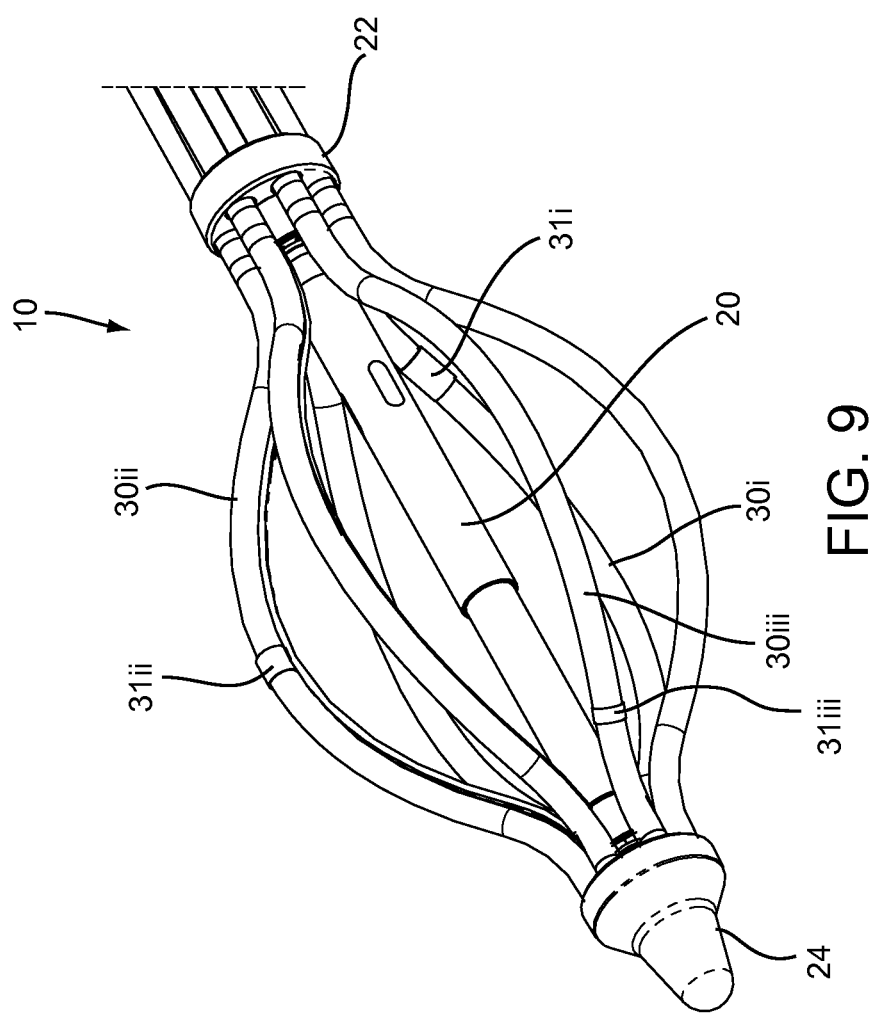
FIG. 9 is a perspective view of another alternative embodiment of an expandable therapy delivery portion of a brachytherapy apparatus including a plurality of markers on catheter tubes for monitoring the apparatus after implantation using external imaging.

Turning to FIG. 9, one or more additional features may be provided on one or more of the elongate members 30, such as any of the embodiments described herein or in the applications incorporated by reference herein. For example, as shown in FIG. 9, a plurality of radiopaque markers 31 may be provided at one or more axial locations on one or more of the elongate members 30, e.g., to facilitate orientation, positioning, and/or otherwise monitoring the apparatus 10 using external imaging. In the exemplary embodiment shown, a first marker 31i may be provided adjacent a proximal end 32 of a first elongate member 30i, a second marker 31ii may be provided at a midpoint of a second elongate member 30ii, and a third marker 31iii may be provided adjacent a distal end 34 of a third elongate member 30iii. Because of the staggered axial placement of the markers 31 relative to one another, the three-dimensional orientation and/or position of the elongate members 30 may be determined from a two-dimensional image, e.g., from fluoroscopy or other x-ray imaging. In addition or alternatively, the markers 31 may have different lengths to facilitate distinguishing them from one another. As shown, the first marker 31i is longer than the second marker 31ii, which is longer than the third marker 31iii, allowing the respective elongate members 30 to be distinguished from one another and more easily identified relative to surrounding tissue and/or within a cavity within which the apparatus 10 has been implanted.

For example, identification of the specific elongate members 30 may facilitate creating a dose plan, e.g., based on CT scan reconstruction of the apparatus 10 after implantation but before delivery of radiation. Identification of the elongate members 30 may also facilitate confirming whether the apparatus 10 has moved, e.g., whether the orientation and/or position of the elongate members 30 has changed between treatments involving multiple visits and/or radiation delivery sessions.

This marking method may facilitate identifying a particular catheter 30 within a patient's body and correlating it to a particular proximal end extending from the patient, e.g., using one or more identifying numbers or other visual markers on the proximal end of the respective catheter 30. For example, alternate catheters, e.g., a second, fourth, and sixth catheter (clockwise around the proximal end of a six catheter apparatus 10), may include numbers or other visual markers that may be associated with respective radiopaque markers. Thus, the location of particular catheter 30 may be identified within the patient's body using the marker 31, and the lumen 36 associated with the particular catheter 30 may be identified, e.g., to facilitate introducing one or more radiation sources therein, as described elsewhere herein.

Alternatively, with continued reference to FIG. 9, the markers 31 may be provided from materials that may facilitate monitoring the elongate members 30 and/or other components of the apparatus 10 using other imaging modalities. For example, the markers 31 may be formed from an echogenic coating or surface treatment, which may enhance identification using ultrasound imaging. In addition or alternatively, the supports 40 of the elongate members 30 may be treated to increase their echogenicity, e.g., by applying a surface finish to Nitinol supports, such as a polymer based coating, physically changing the surface characteristics via bead blasting, and the like.

Returning to FIGS. 1A-2A, with additional reference to FIGS. 3E and 3F, the core member 20 may include telescoping elongate members 50, 60 that allow the proximal and distal hubs 22, 24 to be moved axially towards and/or away from one another. As shown, the core member 20 includes a first or proximal tube 50 including proximal and distal ends 52, 54, and a second or distal tube 60 also including proximal and distal ends 62, 64. The proximal and distal tubes 50, 60 may also include lumens 56, 66 extending between the proximal ends 52, 62 and distal ends 54, 64 and that communicate with one another. Thus, the core member 20 may define a lumen for directly receiving one or more radiation sources (not shown) or for receiving the central catheter tube 81, which may, in turn, receive one or more radiation sources. The proximal and distal tubes 50, 60 may interact with one another, i.e., at distal end 54 and proximal end 62, e.g., to allow the proximal tube 50 to telescope at least partially into the distal tube 60 (or alternatively the distal tube 60 may telescope into the proximal tube 50).

As best seen in FIG. 2B, the distal end 64 of the distal tube 60 is received within or otherwise attached to the distal hub 24. For example, the distal end 64 may be secured to the distal hub 24, e.g., using an interference fit, cooperating connectors, bonding using adhesive, sonic welding, and the like. Thus, the distal tube 60 may remain substantially stationary, e.g., axially and/or rotationally, relative to the distal hub 64 and the distal ends 34 of the elongate members 30.

As shown in FIGS. 2C, 3E, and 3F, the proximal end 62 of the distal tube 60 includes internal threads 63 extending for a predetermined distance along the length of the proximal end 62. Thus, the proximal end 62 may also include an unthreaded region 63a distal to the internal threads 63. The internal threads 63 may be integrally formed in an inner surface of the distal tube 60, may be provided on a separate threaded sleeve received within and/or secured relative to the proximal end 62, and the like. For example, the internal threads 63 may be machined, ground, tapped, or molded on an inside surface of the distal tube 60, or may be machined or molded on an inside surface of a separate sleeve that may be inserted into the distal tube 60 and attached thereto, e.g., using mating connectors, bonding with adhesive, sonic welding, welding, and the like. Alternatively, the internal threads 63 may be provided on a nut insert molded into the distal tube 60, e.g., as best seen in FIG. 3C. Thus, the internal threads 63 may remain substantially stationary, i.e., may not rotate around the longitudinal axis 16 and/or move axially along the longitudinal axis 16. The internal threads 63 may have an axial length of between about 0.050 to 0.250 inch (about 1.25 to 6.25 mm).

As best seen in FIGS. 1B, 2A, 3D, and 6A-6D, the distal tube 60 may be formed from multiple segments attached to one another. For example, the distal tube 60 may include a first tubular segment 60a defining the proximal end 62, e.g., including the internal threads 63 and the unthreaded region 63a, and a second segment 60b extending from the proximal end 62 to the distal end 64. The first and second segments 60a, 60b may be attached to one another, e.g., using mating threads or other cooperating connectors, interference fit, bonding with adhesive, welding, sonic welding, and the like.

For example, as best seen in FIG. 3D, the first and second segments 60a, 60b may be secured together using a lapped joint, adhesive, and the like such that the first and second segments 60a, 60b may be separated from one another upon application of a desired axial force, as explained further below. As shown, the segments 60a, 60b of the distal tube 60 may be connected by a lapped joint 61, which may be created by an interference fit, pressed-fit, adhesive, welding, crimping the first segment 60a around the second segment 60b, and the like. Such a connection or joint may be provided as part of a "bail-out" mechanism, also as described further below. Alternatively, the distal tube 60 may be formed as a single tubular segment extending between the proximal and distal ends 62, 64, thereby defining the lumen 66.

In an exemplary embodiment, shown in FIG. 3A-3D, the apparatus 10 may include three locations that may fail, break, or otherwise separate upon application of a desired force. For example, in FIG. 3B, an insert molded plastic nut or other annular ridge 57 may be provided on the proximal end 52 of the proximal tube 50, and a corresponding shoulder 22a may be provided on the proximal hub 22. If it is desired or necessary to rapidly collapse the elongate members 30, the tubular extensions 33 or other region of the proximal portion 12 may be pulled away from the distal portion 14 with sufficient force to cause the shoulder 22a to push the annular ridge 57 and separate the proximal tube 50 from the distal tube 60, e.g., at the lapped joint 61. In addition, the sleeve defining the internal threads 63 of the distal tube 60 may include a pin 67 that extends into a hole or recess in the distal tube 60, as shown in FIG. 3C. The force sufficient to separate the lapped joint 61 may also cause the pin 67 to be sheared off of the sleeve defining the internal threads 63, thereby allowing the sleeve defining the internal threads 63 to be slid axially within the distal tube 60 without requiring rotation of the proximal tube 50. Once the lapped joint 61 and sleeve defining the internal threads 63 are separated, the proximal tube 50 may be pulled proximally, thereby allowing rapid collapse of the elongate members 30.

Returning to FIGS. 2A-3F, during normal operation (without using the bail-out feature), the proximal tube 50 may be free to rotate about the longitudinal axis 16 within the proximal hub 22, thereby allowing the proximal tube 50 to rotate and thread into or out of the distal tube 60. For example, as shown in FIGS. 2C, 3C, 3E, and 3F, the distal end 54 of the proximal tube 50 may include external threads 55 that interact with the internal threads 63 when the proximal tube 50 is rotated, thereby moving the proximal tube 50 axially relative to the distal tube 60. In an exemplary embodiment, the internal and external threads 63, 55 may be cooperating lead screw thread designs, such as 5-40 ACME double start. Such lead screw mechanisms may allow secured and/or precise actuation of the apparatus 10 with a low overall insertion/removal profile.

For example, the threads 63, 55 may include double pitch threads, i.e., two helical threads in parallel with one another, which allow twice the axial movement per rotation of the proximal tube 50, as compared to a single pitch thread. Such threads may allow rapid relative axial movement between the proximal and distal tubes 50, 60 with minimal amount of rotation. In addition, such threads may provide substantially precise expansion and/or collapse of the elongate members 30, e.g., to expand and/or conform to a body cavity or other treatment site, as described elsewhere herein.

In addition, as best seen in FIGS. 3E and 3F, the proximal tube 50 may include an unthreaded region 55a proximal to the external threads 55. The unthreaded region 55a may have a diameter smaller than the internal threads 63 of the distal tube 60 and/or smaller than the external threads 55, and may have a length substantially equal to or greater than the axial length of the internal threads 63. The proximal tube 50 may include an annular shoulder 53 adjacent the unthreaded region 55a, thereby providing a stop 53 that may also limit axial movement of the proximal tube 50 relative to the distal tube 60. Thus, although the proximal hub 50 is free to rotate within the proximal hub 22, when the proximal tube 50 is rotated to thread the distal end 54 into the proximal end 62 of the distal tube 60, the stop 53 may abut the internal threads 63 during distal movement of the proximal tube 50 relative to the distal tube 60.

As shown in FIGS. 2A and 3B, the annular ridge 57 on the proximal end 52 of the proximal tube 50 may limit and/or couple axial movement of the proximal hub 22 relative to the proximal tube 50. For example, the annular ridge 57 may simply abut the shoulder 22a and/or may be received within an annular groove or pocket (not shown) within the proximal hub 22, thereby directly coupling axial movement of the proximal hub 22 to the proximal tube 50, e.g., when the proximal tube 50 is rotated to move distally and/or proximally relative to the distal tube 60.

Alternatively, it will be appreciated that the proximal and distal tubes 50, 60 may be interchanged, e.g., such that the proximal tube 50 remains substantially stationary and the distal tube 60 is threaded axially relative to the proximal tube 50. In this alternative, the proximal tube 50 may be fixed relative to the proximal hub 22 and the distal tube 60 may be rotated within the distal tube 24. In addition or alternatively, the distal tube may be received in the proximal tube (not shown), and may include external threads that may be coupled to internal threads in the proximal tube (also not shown). In these alternatives, the proximal hub 22 may remain substantially stationary, and the distal hub 24 may be directed proximally to expand the apparatus 10 and distally to collapse the apparatus 10.

With particular reference to FIGS. 1A and 3E, the apparatus 10 may be provided initially with the proximal tube 50 of the core member 20 in its proximal position, i.e., with the proximal and distal hubs 22, 24 spaced furthest apart, thereby providing the elongate members 30 in the collapsed condition. As shown, the elongate members 30 and supports 40 may extend substantially axially along the core member 20, i.e., substantially parallel to the longitudinal axis 16, in the collapsed condition. As shown in FIG. 3E, the external and internal threads 55, 63 may be engaged with one another such that rotation of the proximal tube 50 in a first direction, e.g., clockwise, causes the threads 55, 63 to direct the proximal tube 50 distally.

When the apparatus 10 is initially to be expanded from the collapsed configuration, it may be desirable to maximize contact between the internal an external threads 55,63. For example, it may desirable to have at least four or five turns of the internal thread 63 engaged, e.g., to distribute forces between the threads 55, 63 when the apparatus 10 is initially being expanded. This initial engagement may reduce wear of the threads 55, 63 and/or may reduce the risk of axial misalignment of the proximal and distal tubes 50, 60 when the proximal tube 50 is rotated into the distal tube 60. In the embodiment shown in FIGS. 3E and 6C, the internal threads 63 on the nut are fully engaged with the external threads 55 on the proximal tube 50 in the collapsed configuration. Thus, when the user rotates the proximal tube 50 to expand the apparatus 10, the forces may be distributed over all of the internal threads 63, thereby reducing the risk of damage or misalignment.

As shown in FIG. 2A, the annular ridge 57 on the proximal tube 50 may abut or be disposed within the shoulder 22a in the proximal hub 22 until the proximal tube 50 begins threading into the distal tube 60. Because of the interaction between the annular ridge 57 and the shoulder 22s, rotation of the proximal tube 50 in the first direction causes the proximal hub 22 to be directed distally towards the distal hub 24. As the proximal hub 22 is directed towards the distal hub 24, the elongate members 30 become subjected to an axially compressive force, which causes the elongate members 30 to bow radially outwardly towards the expanded configuration, as shown in FIG. 1B.

As described in the applications incorporated by reference herein, the elongate members 30 may expand into a predetermined shape in the expanded configuration, e.g., due to the supports 40 and/or the configuration of the elongate members 30. For example, the elongate members 30 may be directed into a generally spherical shape, an elliptical shape, and the like, including single or multiple layers, as disclosed in the applications incorporated by reference elsewhere herein. As shown in FIGS. 5A and 5B, as the apparatus 10 is expanded, the axial length "L" between the proximal and distal hubs 22, 24 may be reduced, as can be seen in FIGS. 5A and 5C.

As best seen in FIG. 3F, the proximal tube 50 may be rotated until the external threads 55 pass entirely through the internal threads 63 and into the unthreaded region 63a of the distal tube 60. At substantially the same time, the internal threads 63 enter the unthreaded region 55a on the proximal tube 50. Thus, further rotation of the proximal tube 50 causes the proximal tube 50 to simply spin freely within the distal tube 60 without causing further distal movement of the proximal hub 22. This freedom of motion may provide tactile feedback to the user that the elongate members 30 have been fully expanded to the expanded configuration. In addition, the internal threads 63 may abut the shoulder 53, thereby preventing further distal movement of the proximal tube 50 relative to the distal tube 60.

Optionally, when the internal and/or external threads 63, 55 enter the unthreaded regions 55a, 63a, the user may hear an audible "click" or other audible sound also providing confirmation that the elongate members 30 are fully expanded. For example, one or more features (not shown) may be provided on the internal threads 63, e.g., that may contact the proximal-most thread of the external threads 55, that may "click" if the proximal tube 50 is rotated further to provide feedback to the user. In addition, if desired, one or more features (not shown) may be provided on the internal and/or external threads 63, 55 to provide a similar "click" or other sound when the proximal tube 50 is advanced distally to one or more positions relative to the distal tube 60. For example, the features may be configured to provide a first "click" when the elongate members 30 are expanded less than one hundred percent (100%), e.g., about fifty percent (50%) expanded, and then another "click" when the elongate members 30 are substantially one hundred percent (100%) expanded.

This configuration of the threads 55, 63 may also prevent overexpansion of the elongate members 30. Once the threads 55, 63 disengage, the proximal tube 50 may not be directed distally further, thereby preventing further distal movement of the proximal hub 22. Thus, the relative length and location of the external and internal threads 55, 63 may be selected to provide a desired size and/or shape for the elongate members 30 in the expanded configuration.

Alternatively, it will be appreciated that other mechanisms may be provided for expanding the elongate members 30. For example, the threads 55, 63 may be replaced with a ratchet mechanism (not shown), which may allow the proximal and distal hubs 22, 24 to be directed towards one another in a stepwise manner, thereby causing the elongate members 30 to expand radially outwardly. In a further alternative, a cable or other actuator (not shown) may extend from the distal hub 24 through the proximal portion 12, which may be pulled to direct the distal hub 24 proximally towards the proximal hub 22, i.e., to expand the elongate members 30. However, a cable or other actuator extending to the proximal portion 12 may require maintaining axial force to prevent the elongate members 30 from being released and collapsing. Thus, the threads 62, 55 may prevent accidental release and/or collapsing of the elongate members 30 during use.

With continued reference to FIGS. 1A, 1B, 3E, and 3F, when it is desired to collapse the elongate members 30, the proximal tube 50 may be rotated in a second opposite direction, e.g., counterclockwise. The external threads 55 may reengage the internal threads 63, and then thread the external threads 55 proximally, thereby directing the proximal hub 22 proximally. Optionally, the internal threads 63 may include a chamfer or other feature (not shown), which may facilitate reengaging the threads 63, 55 when the external threads 55 are in the unthreaded region 63a. As the proximal hub 22 is directed proximally, the elongate members 30 and supports 40 may be pulled back radially inwardly towards the collapsed configuration, as shown in FIG. 1A.

If the annular ridge 57 on the proximal tube 50 is not directly coupled to the proximal hub 22, e.g., is disposed proximal to the proximal hub 22, the proximal tube 50 may not pull the proximal hub 22 proximally. In this embodiment, the supports 40 and/or the elongate members 30 themselves may be sufficiently resiliently biased towards the collapsed configuration such that they push the proximal hub 22 proximally once the proximal hub 22 is no longer abutted by the stop 53. Optionally, as can be seen in FIG. 3E, the external threads 55 may be threaded proximally completely through the internal threads 63 such that the threads 55, 63 are disengaged when the apparatus 10 is fully collapsed. If desired, the elongate members 40 may be under slight tension in this position such that further rotation of the proximal tube 50 (to collapse the apparatus 10) may cause the threads to "click" or provide other audible feedback to indicate that the threads 55, 63 have been fully disengaged and/or the apparatus 10 has been fully collapsed. Such tension may also facilitate reengaging the threads 55, 63 again if it is desired to expand the apparatus 10. This configuration may also prevent stretching the elongate members 30 beyond a desired collapsed configuration.

To facilitate expansion and collapse of the apparatus 10, the expansion tool 70 may be coupled to the proximal end 52 of the proximal tube 50. For example, the proximal end 52 of the proximal tube 50 may include external threads, a hex head, or other connector (not shown), which may be used to connect the expansion tool 70 to the apparatus 10. Thus, the expansion tool 50 may be connected to the apparatus 10 during expansion of the elongate members 30, whereupon the expansion tool 50 may be removed, leaving the elongate members 30 expanded, e.g., to allow several treatment sessions. When it is desired to remove the apparatus 10, the expansion tool 70 may be reconnected to the apparatus 10, e.g., to the proximal tube 50, and used to collapse the elongate members 30, whereupon the apparatus 10 may be removed from the patient's body.

With additional reference to FIG. 2A, the expansion tool 70 may include an elongate body including a proximal end 72, a distal end 74, and a lumen 76 extending therebetween. A handle 78 may be provided on the proximal end 72, e.g., to facilitate manipulation and/or rotation of the expansion tool 70.

During use, the expansion tool 70 may be inserted between the elongate members 40 and engaged with the connector(s) on the proximal end 52 of the proximal tube 50 of the core member 20. For example, as explained above, a shaft 80 may be coupled to the core member 20, e.g., extending from the proximal hub 22, that includes a distal end 84 disposed adjacent the proximal end 52 of the proximal tube 50. In this embodiment, as shown in FIG. 2A, the distal end 74 of the expansion tool 70 may be inserted over the central catheter tube 81 and into the lumen 86 of the shaft 80.

The expansion tool 70 may be advanced until the distal end 74 engages with the proximal end 52 of the proximal tube 50 of the core member 20. For example, the distal end 74 and the proximal end 52 may include mating threads, a male-and-female keyed connectors, and the like (not shown). Thereafter, when the expansion tool 70 is rotated, the proximal tube 50 of the core member 20 may then also be rotated, and thereby translated axially as described elsewhere herein.

Optionally, as shown in FIGS. 1A and 1B, a handle 83 may be provided on the proximal end 82 of the shaft 80, e.g., to facilitate manipulation of the shaft 80 and/or connection of the expansion tool 70. In addition or alternatively, as shown in FIGS. 3G and 3H, one or more visual indicators 85 may be provided on the central catheter tube 80, e.g., to indicate when the elongate members 30 are expanded. For example, as shown in FIG. 3G, a first band or other visual marker 85a may be provided that is exposed when the expansion tool 70 is coupled to the apparatus 10, e.g., to the core member 20 (not shown), as described above. As the expansion tool 70 is rotated to expand the apparatus 10, the expansion tool 70 may be directed distally and/or the central catheter 81 may be directed proximally, thereby exposing one or more additional markers 85b, 85c proximal to the handle 78 of the expansion tool 70.

Thus, the markers 85 may provide visual confirmation to the user that the elongate members 30 are expanded to a predetermined extent. For example, a second marker 85b may become exposed when the elongate members 30 are expanded less than one hundred percent (100%), e.g., about fifty percent (50%), and a third marker 85c may become exposed when the elongate members are expanded substantially one hundred percent (100%), as shown in FIG. 3H.

In addition or alternatively, the expansion tool 70 itself may include one or more indicators to facilitate determining when the apparatus 10 is expanded and/or collapsed. For example, as best seen in FIGS. 1A, 1B, 2A, 3G, and 3H, the handle 78 may include a tab or other visual indicator 78a extending radially from the handle 78. The indicator 78a may allow a user to monitor the number of turns of the expansion tool 70, which may correspond to a predetermined expansion of the elongate members 30. Thus, the user may rotate the handle 78 a desired number of turns, thereby expanding the apparatus 10 to a corresponding diameter or other expanded shape.

Figure 11:
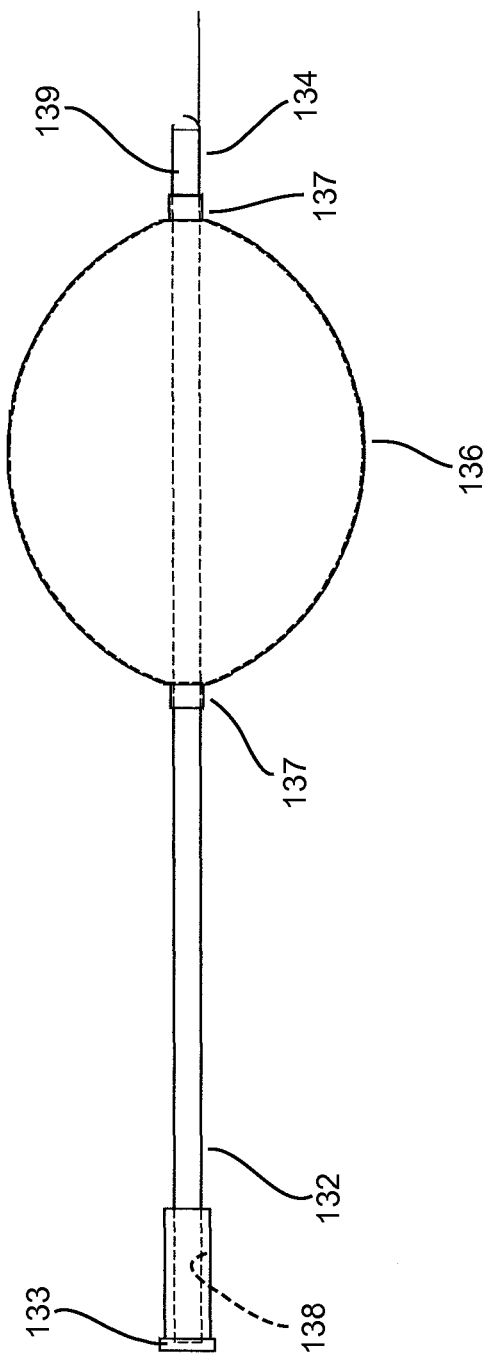
FIG. 11 is a side view of a balloon catheter for preparing a body cavity before delivering brachytherapy.

Optionally, before introducing the apparatus 10 into a body cavity, it may be desirable to dilate or otherwise expand the body cavity. Turning to FIG. 11, a prep catheter 130 is shown that includes a proximal end 132, a distal end 134 sized for introduction through a tissue tract into the body cavity (not shown), and a balloon 136 on the distal end 134. The catheter 130 may include an inflation lumen 138 extending distally from the proximal end 132 and communicating with the interior of the balloon 136. In the embodiment shown, a one-way syringe activated valve 133 may be provided on the proximal end 132, which may opened using a syringe to deliver inflation media and/or remove inflation media from the balloon 136. The balloon 136 may be formed from semi-compliant material such that, when the balloon 136 is inflated, e.g., with saline or other inflation media, the balloon 136 may grow to different volumes with different fill volumes of saline, yet the balloon material may be sufficiently rigid to provide substantial dilating power to the surrounding tissue. In an exemplary embodiment, the balloon 136 may have a length of between about three to six centimeters (3-6 cm), a maximum expanded diameter of between about three to five centimeters (3-5 cm), a durometer or softness between about 85-95, e.g., about 90 Shore A, and/or a wall thickness of one to two thousandths of an inch (0.025-0.050 mm).

Optionally, the catheter 130 may include one or more markers, e.g., radiopaque marker bands 137 on either end of the balloon 136, e.g., to facilitate monitoring the catheter 130 using external imaging. For example, the marker bands 137 may allow the location of the balloon 136 relative to the body cavity to be determined before expanding the balloon 136, thereby ensuring that the balloon 136 is properly positioned within the body cavity. The catheter body may include a substantially rigid distal tip 139 and a semi-rigid and/or substantially flexible portion proximal to the distal tip 139. The catheter 130 may have an overall length of between about seventeen to twenty five centimeters (17-25 cm), e.g., about twenty centimeters (20 cm), with the distal tip having a length of between about 0-1.0 cm, e.g., about seven millimeters (7 mm).

Figure 12:
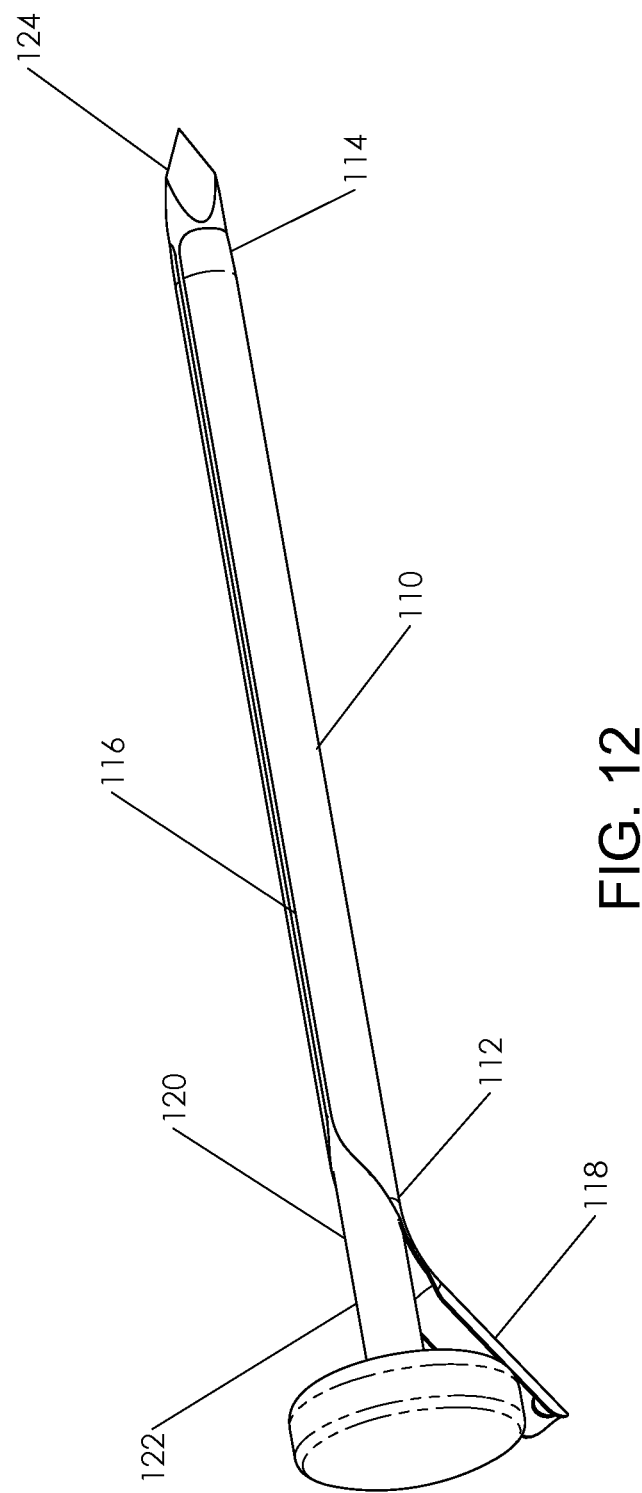
FIG. 12 is a perspective view of an introducer sheath for facilitating introduction of a brachytherapy apparatus into a body cavity, carried on an obturator.

Turning to FIG. 12, if desired, an introducer sheath 110 may be provided to facilitate introduction of the apparatus 10 into a treatment site, e.g., into a body cavity or other tissue structure (not shown). The introducer sheath 110 generally includes a proximal end 112, a distal end 114 sized for introduction into a tissue tract, and a slit 114 extending therebetween. Optionally, the sheath 110 may include a tab, handle, or other feature 118 extending from the proximal end 112, e.g., to facilitate removal and/or other manipulation of the introducer sheath 110. As shown if FIG. 12, the entire sheath 110 may be made from one segment of extruded tubing. The sheath 110 may be formed from a semi-rigid or flexible material, e.g., FEP, including side edges defining the slit 114 that may have a gap of several millimeters, or may abut or at least partially overlap one another. A trocar, obturator, needle, or other elongate member 120 may be disposed within the sheath 110, e.g., including a proximal end 122 adjacent the proximal end 112 of the sheath 110, and a sharpened distal end 124 extending beyond the distal end 114 of the sheath.

The sheath 110 may have a diameter or other cross-section sufficient to receive the apparatus 10 in the collapsed condition, e.g., after removing the trocar 120. Although the side edges defining the slit 114 may be biased to abut or overlap one another, the sheath material may be sufficiently flexible to allow the sheath 110 to be pulled proximally and/or laterally from around the apparatus 110, trocar 120, and/or other device received within the sheath 110. Thus, the side edges defining the slit 114 may be forced apart open the slit 114 and facilitate removal of the sheath 110.

Figure 13A:
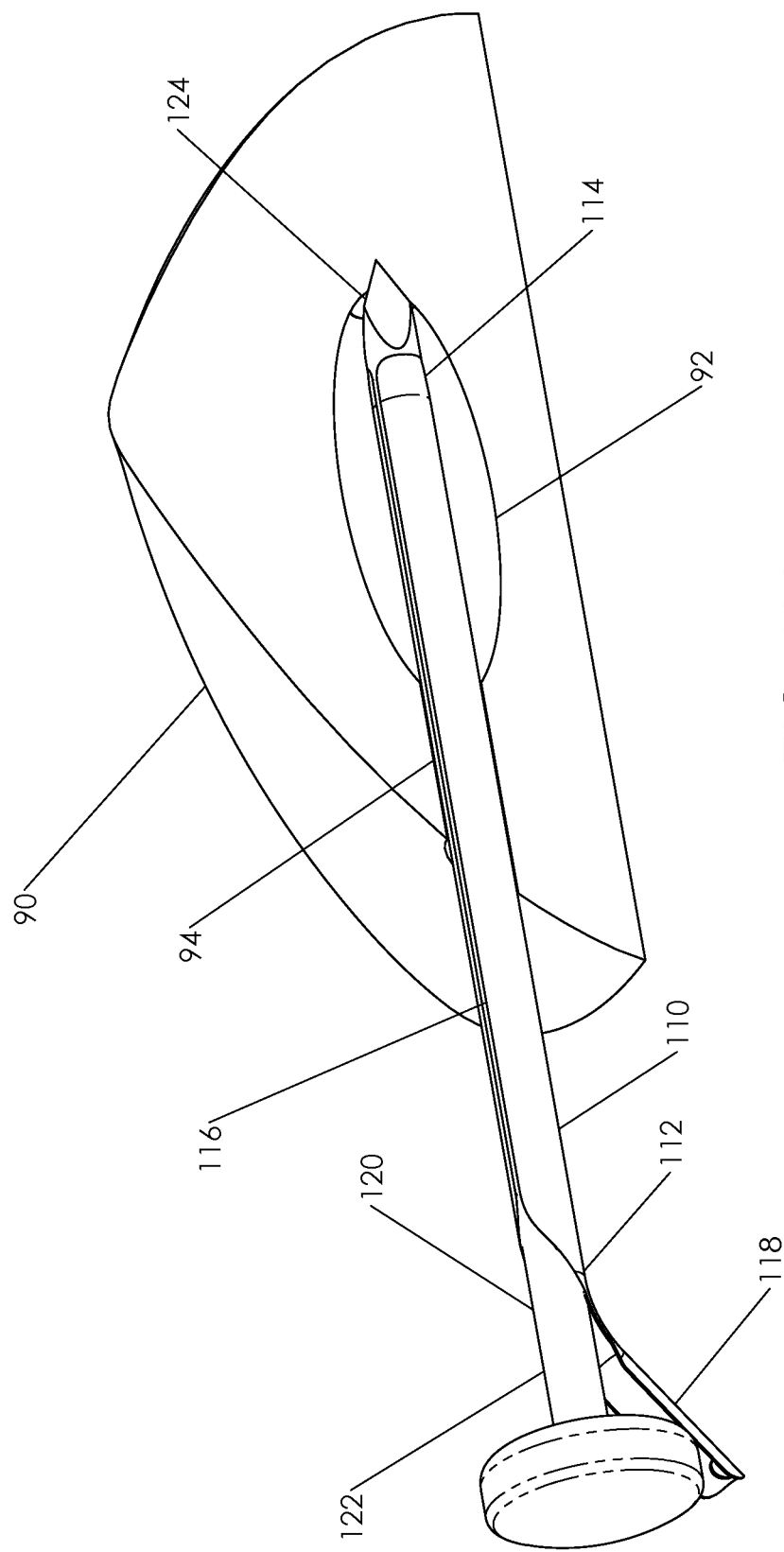
FIGS. 13A-13F show a method for introducing a brachytherapy apparatus into a lumpectomy cavity of a breast using the introducer sheath of FIG. 12.
Figure 13B:
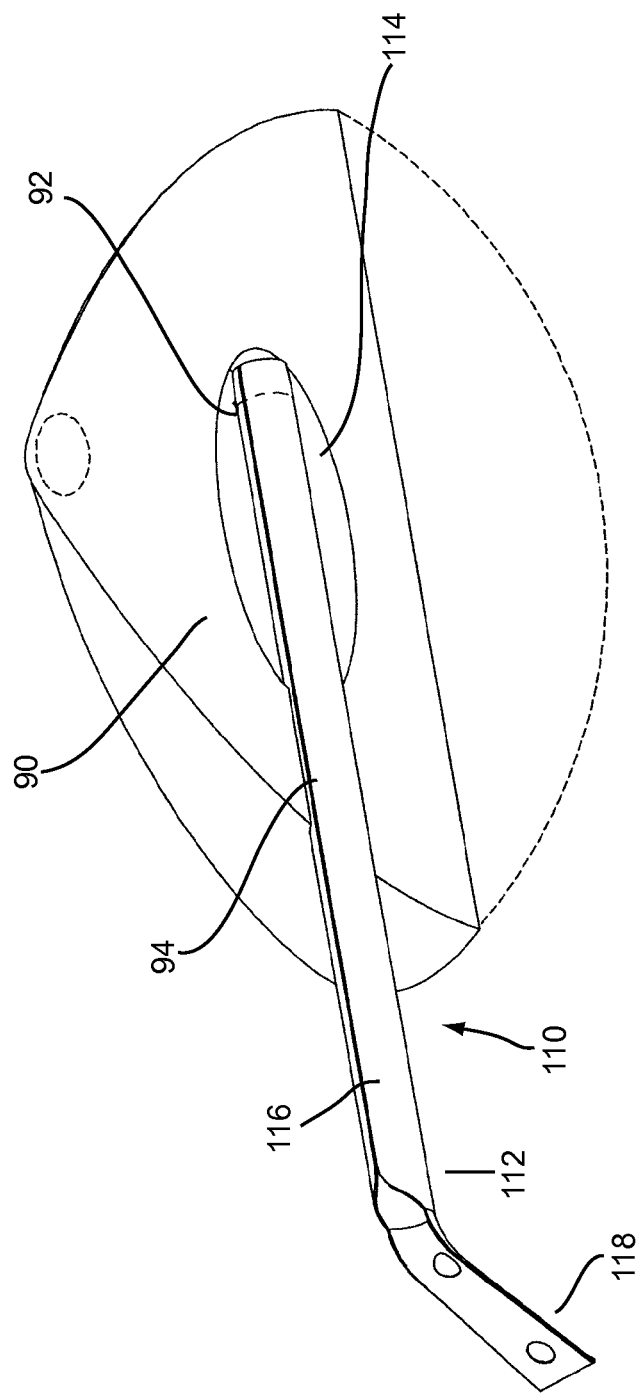

Turning to FIGS. 13A-13F, the apparatus 10 may be used for brachytherapy treatment within a tissue structure, for example within a breast 90. As shown, the breast 90 may have a cavity (e.g., a lumpectomy cavity 90) formed therein, e.g., by removal of cancerous tissue. If the introducer sheath 110 is used, the introducer sheath 110 and trocar 120 may be introduced into the cavity 92, as shown in FIG. 13A. For example, if the trocar 120 includes a sharpened distal end 124, the introducer sheath 110 and trocar 120 may be advanced directly through tissue, thereby creating a tract 94 communicating with the cavity 92. Alternatively, the tract 94 may be created in advance, e.g., using a needle or other device (not shown).

As shown in 13B, the trocar 120 may then be removed, leaving the introducer sheath 110 to provide a path through the tissue of the breast 90 into the cavity 92. Optionally, if desired, the inner surface of the introducer sheath 1 10 may include lubricious material to facilitate introducing devices therethrough.

Figure 13C:
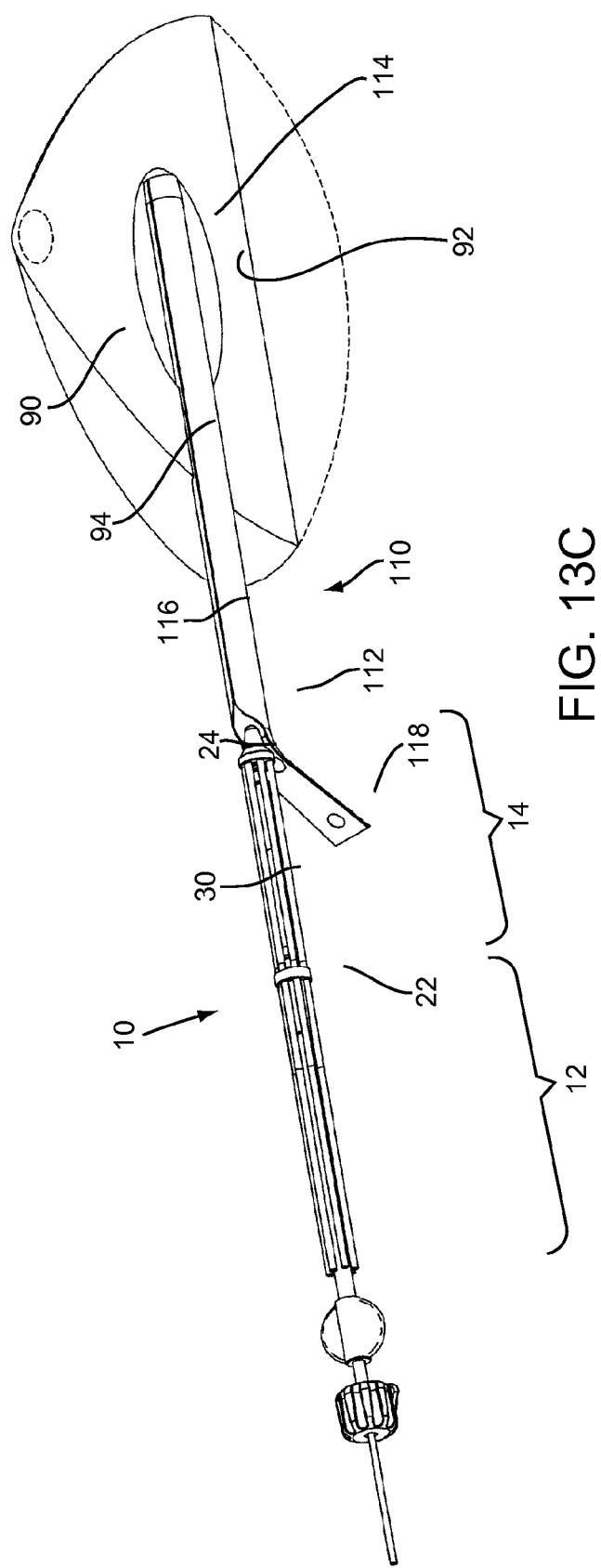
Figure 13D:
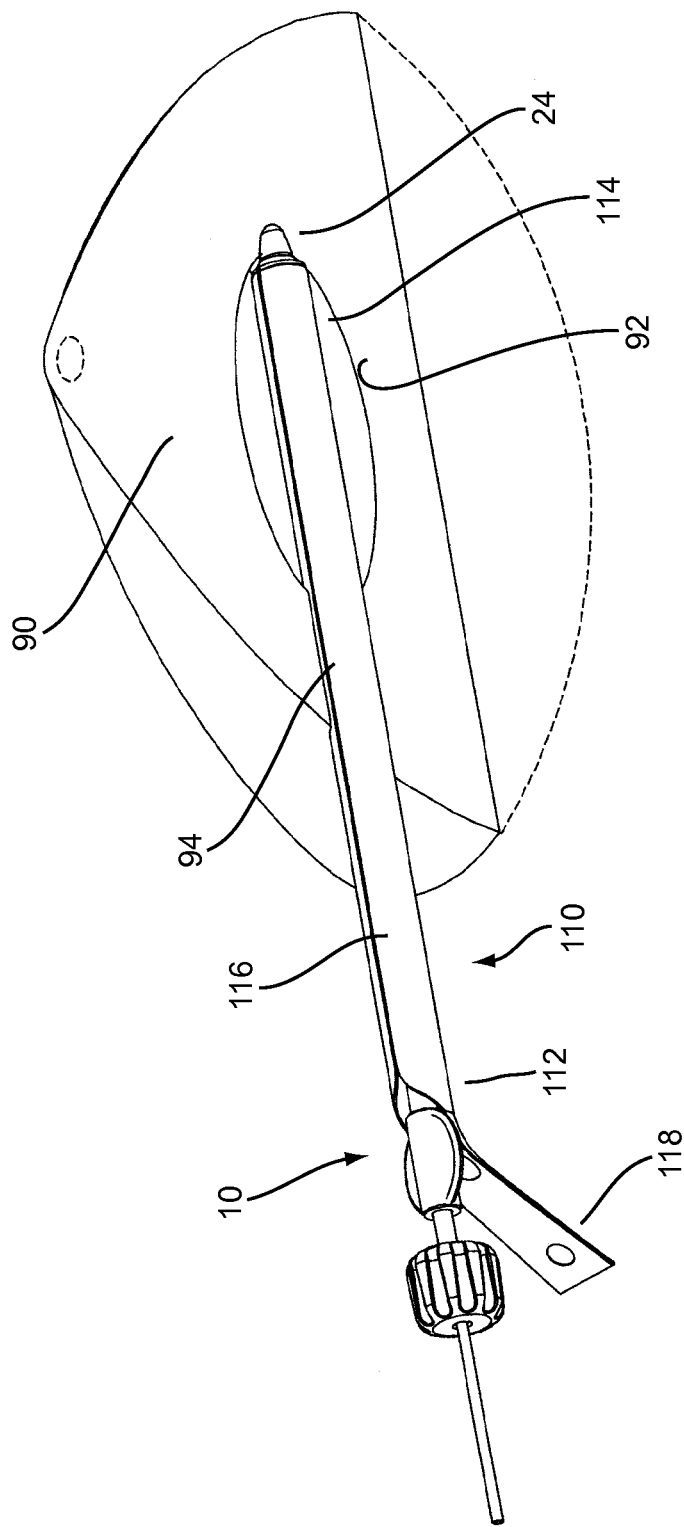

Turning to FIGS. 13C and 13D, the apparatus 10 is shown being inserted through the introducer sheath 110 in the collapsed configuration, e.g., until the distal hub 24 is disposed within the cavity 92. Alternatively, the apparatus 10 may be inserted directly through an existing incision, e.g., the incision used to perform the lumpectomy, or via a new incision created for delivering the apparatus 10, and/or may be advanced directly through tissue, e.g., if the distal hub 24 includes a sharpened tip (not shown), as described in the applications incorporated by reference herein.

Figure 13E:
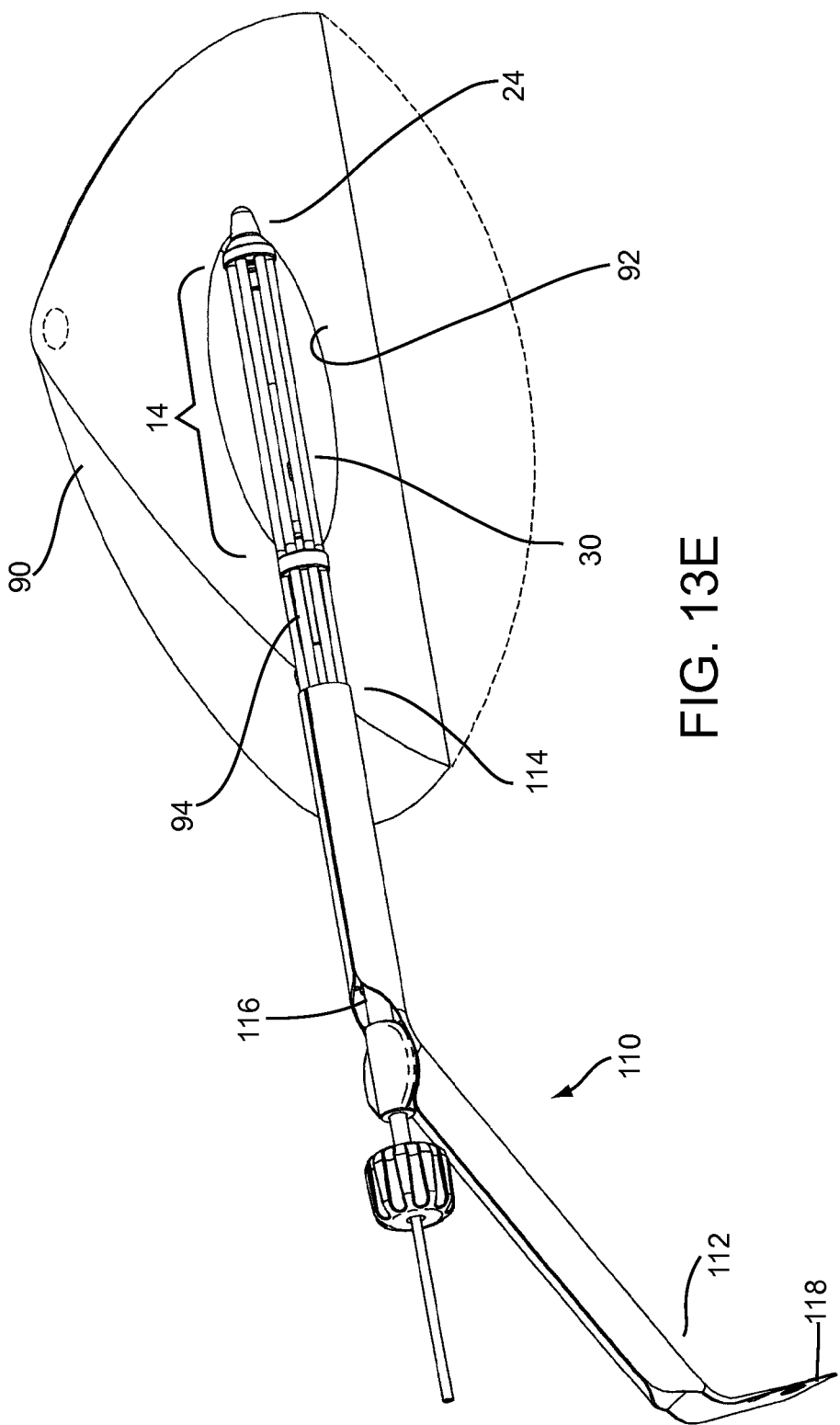
Figure 13F:
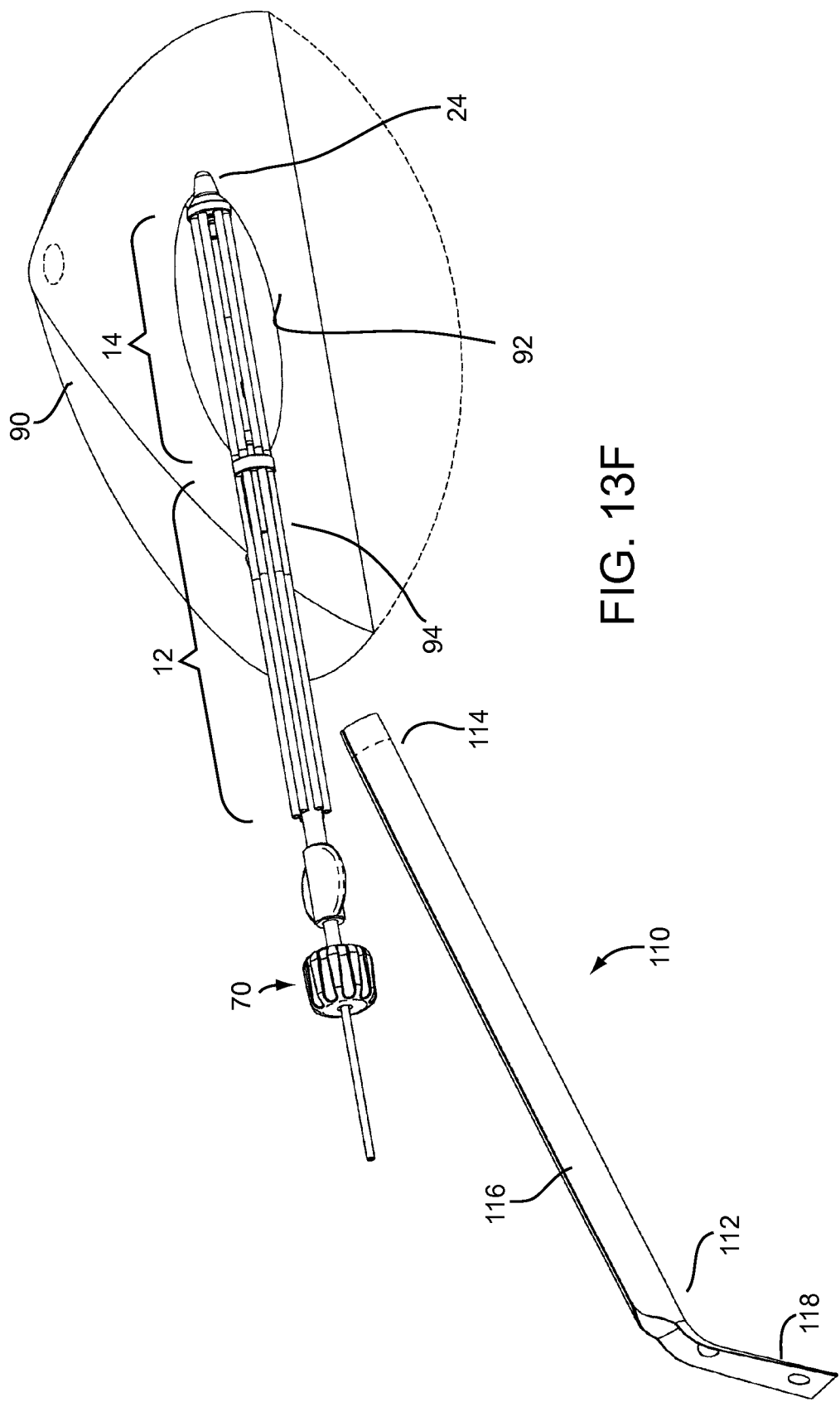

During insertion, the apparatus 10 may be positioned to place the elongate members 30 (in the collapsed configuration) entirely within the cavity 92, as shown in FIG. 13E. Turning to FIG. 13F, once the apparatus 10 is positioned within the cavity 92, the introducer sheath 110 may be removed from around the apparatus 10. As shown, the introducer sheath 110 may be pulled transversely away from the apparatus 10, thereby causing the side edges defining the slit 116 to separate and pass around the apparatus 10.

Turning to FIG. 13F, the apparatus 10 is shown with the introducer sheath 110 completely removed, the distal portion 14 of the apparatus 10 positioned completely within the cavity 92, and the proximal portion 12 extending from the cavity 92, through the tract 94, and out of the breast 90. Thus, the apparatus 10 is ready for expansion and delivery of radiation. If the expansion tool 70 is separate from the apparatus 10, the expansion tool 70 may connected to the apparatus 10. As shown in FIGS. 13A-13F, the expansion tool 70 is provided already coupled to the apparatus 10, e.g., as described elsewhere herein.

The expansion tool 70 may then be rotated in a first direction to direct the proximal hub 22 distally relative to the distal hub 24, thereby causing the elongate members 30 to bow outwardly within the cavity, as shown in FIGS. 1B and 4A. When the apparatus 10 is directed to the expanded configuration, the elongate members 30 may at least partially direct tissue surrounding the cavity outwardly and/or the tissue may invaginate between adjacent elongate members 30, as disclosed in the applications incorporated by reference herein. Optionally, the elongate members 30 and/or the distal portion 14 may include one or more extensions, membranes, or other features to shape the cavity in a desired manner, also as disclosed in the applications incorporated by reference herein.

The lengths of the elongate members 30 may be selected to be compatible with common commercially available remote afterloader transfer tubes (not shown), such as those available from Varian and Nucletron. When the elongate members 30 have diameters and/or lengths compatible with the afterloader, it may reduce the physicist's efforts during dose planning.

Optionally, thereafter, the apparatus 10 may be secured relative to the target tissue region to prevent subsequent migration. Alternatively, the elongate members 30 may sufficiently engage the surrounding tissue to prevent substantial migration. If the apparatus 10 is to remain within the target tissue region for an extended period of time, the expansion tool 70 may be removed from the apparatus 10.

One or more radiation sources (not shown) may then be directed into the lumens 36 of the elongate members 30 to deliver radiation to the tissue surrounding the cavity. Thus, the elongate members 30 may define pathways for receiving radiation source(s). If the central catheter tube 81 is provided or the core member 20 includes a lumen, one or more radiation sources may also be directed into the lumen of the central catheter tube 81 and/or core member 20. Alternatively, the elongate members 30 and/or core member 20 may include other features providing pathways extending between the proximal and distal portions 12, 14 of the apparatus 10. For example, the elongate members 30 may include grooves or tracks (not shown), which may receive one or more sources of radiation, as described in the applications incorporated by reference herein.

In an exemplary procedure, a plurality of LDR sources may be delivered into the elongate members 30 and/or core member 20, and remain indwelling for a predetermined time. For example, individual pods or other radiation sources may be loaded into respective elongate members 40 simultaneously or sequentially, thereby providing a three dimensional array of seeds or radiation sources that may remain in the target location for an extended period of time. The seeds may be spaced apart on each pod or have different radioactive intensities, according to the dose plan. For example, the seeds in different portions of the array may also have different lengths and/or spacing along respective elongate members 10 such that the array is substantially asymmetrical, e.g., radially and/or axially relative to a central axis of the apparatus 10.

Alternatively, one or more HDR sources may be delivered sequentially into the elongate members 30 and/or core member 20 according to a desired dose plan, as described elsewhere herein. For example, an HDR source may be introduced into a first elongate member 30, advanced to a first position, and maintained at the first position for a predetermined time. The HDR source may then be advanced and/or retracted to a second position, and maintained there for a predetermined time, etc. The HDR source may then be removed from the first elongate member 30, and then introduced sequentially into each of the other elongate members 30 in a similar manner. In a further alternative, one or more radiation sources may be preloaded or secured within the elongate members 30 before introduction into the cavity. Additional information on use of the apparatus 10 may be found in the applications incorporated by reference herein.

At the completion of brachytherapy treatment, the apparatus 10 may be returned to its collapsed configuration, and the apparatus 10 removed from the breast via the insertion incision.

Before treating the patient, it may be desirable to create a dose plan to determine the course of treatment. Dose planning may be accomplished using a variety of imaging methods (e.g., CT or ultrasound) and/or using dose planning software for either HDR or LDR applications. The timing and general scenario of the dose planning process is at the discretion of the clinical physicist/oncologist. However, one such scenario may include placing the apparatus 10 into the target tissue region and actuating the distal portion 14 into the deployed configuration. Then, with the aid of imaging (e.g., CT), both the target tissue region and the position of the elongate members 30 may be delineated. A dose plan may then be developed and, if desired, modified as configuration adjustments are made to the apparatus 10 and/or the elongate members 30.

Turning to FIGS. 16A-18D, another embodiment of an expandable brachytherapy apparatus 210 is shown that includes a proximal or tail portion 212, and a distal or therapy delivery portion 214, defining a longitudinal axis 216 extending therebetween, generally similar to the previous embodiments. The distal portion 214 of the apparatus 210 may be movable between a collapsed configuration, e.g., as shown in FIGS. 16A-16D, for introduction through a tissue tract to a target location, and a fully deployed or expanded configuration, e.g., as shown in FIGS. 18A-18D, for providing a three dimensional array of pathways at the target location, also generally similar to the previous embodiments and as described further below.

For example, the apparatus 210 may include an expansion tool 270, which may be coupled to the apparatus 210 for expanding and/or collapsing the distal portion 214, e.g., as described above for the previous embodiments. Optionally, the apparatus 210 may be part of a system, e.g., including a tubular delivery device, such as a catheter, cannula, trocar, obturator, and/or needle (also not shown), also similar to the previous embodiments.

Similar to the previous embodiments, the apparatus 10 includes an elongate core member 220 and a plurality of elongate members or catheters 230 disposed around the core member 220 and extending between a proximal hub 222 and a distal hub 224. The core member 220 may be a substantially rigid member extending between the proximal and distal hubs 222, 224 yet compressible and/or extendable axially to direct the proximal and distal hubs 222, 224 towards and/or away from one another, e.g., a telescoping member, similar to the previous embodiments.

The catheters 230 include a proximal end 232, a distal end 234, and a lumen 236 extending therebetween (shown in FIGS. 16C, 17C, and 18C), e.g., for receiving a radiation source (not shown). The proximal ends 232 may be received in, through, and/or coupled to the proximal hub 222 and the distal ends may be received in, through, and/or coupled to the distal hub 224, e.g., as described elsewhere herein and in the applications incorporated by reference herein. The catheters 230 may be constructed and/or include features similar to any of the embodiments described elsewhere herein and/or in the applications incorporated by reference herein.

Tubular extensions 233 may also be received in and/or coupled to the proximal hub 222, coupled directly to the proximal ends 232 of the catheters 230, and/or integrally molded or otherwise formed with the catheters 230, e.g., extending proximally from the proximal hub 222. Each tubular extension 233 may include an opening (not shown) providing access into a respective lumen, e.g., through the tubular extension 233 into a respective catheter 230, for receiving a radiation source, as described elsewhere herein. The tubular extensions 233 may remain substantially free relative to one another or may be at least partially constrained relative to one another, e.g., by a collar 238, similar to previous embodiments. The core member 220 may be coupled to a flexible shaft 280 extending proximally from the proximal hub 222 or collar 238. Thus, the shaft 280 and the tubular extensions 233 may substantially define the proximal portion 212 of the apparatus 210.

The shaft 280 may include a lumen (not shown) sized to receive the expansion tool 270 and/or a central catheter tube (also not shown). The central catheter tube may extend through the lumen into the core member 220, and optionally into the distal hub 224, e.g., providing a lumen for receiving a radiation source (not shown), similar to the previous embodiments. Alternatively, as can be seen in FIG. 16C, the core member 220 may include a lumen 266 (without necessarily including a central catheter tube) for receiving a radiation source.

Unlike the previous embodiments, the apparatus 210 includes a guide hub 290 on the core member 220 between the proximal and distal hubs 222, 224. The guide hub 290 may be substantially fixed to the core member 220, e.g., attached to a distal and/or outer telescoping tube of the core member 220, for example, by bonding with adhesive, interference fit, fusing, welding, and the like. Alternatively, the guide hub 290 may be integrally molded, machined, or otherwise formed with the core member 220 (or a component of the core member 220).

For example, the guide hub 290 may be a molded plastic body slid around the core member 220 during assembly of the apparatus 210 and fixed at a desired location, e.g., substantially midway between the proximal and distal hubs 222, 224. The guide hub 290 includes a plurality of grooves or other recesses 292 that extend substantially parallel to the longitudinal axis 216 of the apparatus 210 and that are spaced apart around the circumference of the guide hub 290. As shown in FIG. 16C, the guide hub 290 includes six grooves 292 corresponding to respective catheters 230, e.g., such that the catheters 230 are seated in the grooves 292 when the distal portion 214 is in its collapsed configuration, as shown in FIGS. 16A-16D. Thus, if the apparatus 210 includes more or fewer catheters 230, the number of grooves 292 may correspond to the number of catheters 230.

As best seen in FIG. 16C, each groove 292 includes a rounded bottom surface 292a and opposing side walls 292b extending radially outwardly from the bottom surface 292a. As shown, the side walls 292b of each groove 292 are substantially parallel to one another and are spaced apart by a distance slightly greater than the outer diameter of the catheters 230. Alternatively, the side walls 292b may not be substantially parallel to one another, e.g., extending radially outwardly relative to the central longitudinal axis 216 of the apparatus 210. The side walls 292b may be prevent substantial lateral movement of the catheters 230 during initial expansion, i.e., until the catheters 230 exit the grooves 292.

The bottom surfaces 292a of the grooves 292 may be spaced apart from the central longitudinal axis 216 by a predetermined distance such that the catheters 230 do not extend substantially parallel to the longitudinal axis 216 in the collapsed configuration. For example, as shown in FIG. 16B, when the distal portion 214 of the apparatus 210 is in the collapsed configuration, the proximal and distal ends 232, 234 of the catheters 230 may be disposed closer to the central longitudinal axis 216 than intermediate regions 235. Thus, the catheters 230 may be arched outwardly slightly between the proximal and distal ends 232, 234 in the collapsed configuration due the intermediate regions 235 being received in the grooves 292 and abutting the bottom surfaces 292a. Alternatively, the size of the grooves 292 may be such that the catheters 230 extend substantially parallel to the longitudinal axis 216 in the collapsed configuration (not shown).

This arched shape may facilitate proper expansion of the catheters 230, e.g., as the proximal and distal hubs 222, 224 are directed towards one another as described above. The catheters 230 may bend outwardly as the proximal and/or distal hubs 222, 224 are moved in the same radial direction as the initial arching, thereby reducing lateral movement of the intermediate regions 235 of the catheters 230 (i.e., in a direction about the circumference of the distal portion 214). Thus, in an alternative embodiment, the grooves 292 may be eliminated if the diameter or other cross-section of the guide member 290 provides sufficient initial arching of the catheters 230 in the collapsed configuration. However, the side walls 292b of the grooves 292 may also prevent substantial lateral movement during initial expansion since lateral movement of the catheters 230 are also limited by the spacing of the side walls 292b.

As can be seen in FIGS. 17A-17D, the catheters 230 remain substantially evenly spaced apart from one another about the circumference of the distal portion 214 during initial expansion while the intermediate regions 235 remain within the grooves 292. The depth of the grooves 292 may be sufficient deep such that, once the intermediate regions 235 exit the grooves 292, as shown in FIGS. 18A-18D, the catheters 230 are arched or bent sufficiently that they may resist lateral movement.

This resistance to lateral movement may be particularly useful when the apparatus 210 is being deployed within a relatively small cavity. The walls of a relatively small cavity may resist expansion of the catheters 230 and may apply localized compressive forces to different regions of the catheters 230 as they move towards the expanded configuration. Thus, the initial guidance of the catheters 210 may ensure a substantially symmetrical expansion of the catheters 230 despite localized resistance by different portions of the cavity walls. For example, both a substantially even arched shape along the length of the catheters 230 between the proximal and distal ends 232, 234, and about the circumferential spacing of the catheters 230 relative to one another)

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A brachytherapy treatment apparatus, comprising:
   an elongate core member comprising a proximal end and a distal end configured for introduction into a tract through tissue, the proximal and distal ends defining a longitudinal axis;
   a distal hub coupled to the distal end of the core member;
   a proximal hub on the proximal end of the core member, at least one of the proximal hub and the distal hub movable axially relative to the other of the proximal hub and the distal hub;
   a plurality of elongate members coupled to the proximal and distal hubs and extending between the proximal and distal ends of the core member, the elongate members movable from a collapsed configuration extending substantially parallel to the longitudinal axis for introduction through a tissue tract to a target location, and an expanded configuration when the proximal hub is directed distally relative to the distal hub, the elongate members comprising pathways for receiving a source of radiation therealong;
   tubular extensions extending proximally from the proximal hub and communicating with respective pathways for directing a source of radiation into the elongate members; and
   a release mechanism distal to proximal ends of the tubular extensions on at least one of the proximal hub and the core member adjacent the proximal hub for irreversibly disengaging the proximal hub from the core member to allow rapid collapse of the elongate members from the expanded configuration.

2. The apparatus of claim 1, wherein the core member comprises first and second telescoping tubes, the first tube coupled to the proximal hub and the second tube coupled to the distal hub such that rotation of the first tube relative to the second tube causes the proximal hub to move distally to direct the elongate members towards the expanded configuration.

3. The apparatus of claim 2, wherein the first and second tubes are telescopingly coupled by mating threads, and wherein the threads are disengaged when the first tube is rotated sufficiently to direct the elongate members to the expanded configuration, thereby limiting further distal movement of the proximal hub.

4. The apparatus of claim 3, wherein at least one of the first and second tubes comprises a stop to prevent further distal movement of the first tube relative to the second tube when the elongate members are directed to the expanded configuration, thereby preventing overexpansion of the elongate members.

5. The apparatus of claim 2, wherein the release mechanism comprises features on one of the proximal hub and the first tube that are disengaged upon application of a desired axial force to disengage the proximal hub and allow the proximal hub to be pulled proximally without rotation to rapidly collapse the elongate members from the expanded configuration towards the collapsed configuration.

6. The apparatus of claim 2, wherein the release mechanism comprises a retaining ring disposed around the first tube to prevent proximal movement of the proximal hub relative to the first tube unless a predetermined axial force is applied to at least one of the proximal hub and the first tube.

7. The apparatus of claim 1, wherein the core member comprises a pathway for receiving a source of radiation.

8. A method for brachytherapy treatment of tissue within a body, comprising:
   creating a tract through tissue to a target location adjacent to a cavity;
   advancing a distal portion of an elongate body carrying a plurality of elongate members through the tract into the target location with the elongate members in a collapsed configuration wherein the elongate body comprises a proximal hub that is movable axially relative to the elongate body when an expansion tool is rotated for directing the elongate members to an expanded configuration;
   directing the elongate members to the expanded configuration at the target location to position the elongate members away from a central axis;
   delivering radiation to the target location to treat tissue at the target location, wherein directing the elongate members to the expanded configuration comprises rotating the expansion tool in a first direction, and wherein, upon directing the elongate members to the expanded configuration, threads on the distal portion are disengaged such that further rotation of the expansion tool in the first direction no longer expands the elongate members; and
   disengaging the proximal hub from the elongate body, and pulling the proximal hub without rotation to collapse the elongate members.

9. The method of claim 8, wherein a stop is contacted after the expansion tool is rotated to direct the elongate members to the expanded configuration to prevent further expansion of the elongate members.

10. A system for brachytherapy treatment of tissue adjacent a cavity within a body, comprising the apparatus of claim 1, the system further comprising:
    a prep catheter comprising a proximal end, a distal end sized for introduction through the tissue tract into a body cavity, and an expandable member on the prep catheter distal end for dilating tissue surrounding the body cavity before introducing the apparatus therein.

11. A method for brachytherapy treatment of tissue, comprising:
    creating a tract through tissue to a target location adjacent to a cavity;
    introducing a distal end of a prep catheter through the tract into the cavity;
    expanding an expandable member on the distal end of the prep catheter within the cavity;
    removing the prep catheter;
    advancing a distal portion of an elongate body carrying a plurality of elongate members through the tract into the target location with the elongate members in a collapsed configuration;
    rotating an expansion tool in a first direction to direct the elongate members to an expanded configuration at the target location to position the elongate members away from a central axis, wherein, upon reaching the expanded configuration, threads on the distal portion are disengaged such that further rotation of the expansion tool in the first direction no longer expands the elongate members; and delivering radiation to the target location to treat tissue at the target location.

12. A system for brachytherapy treatment of tissue adjacent a cavity within a body, comprising the apparatus of claim 1, the system further comprising:
an introducer sheath comprising a proximal end, a distal end sized for introduction through a tissue tract into a body cavity, and defining a lumen therebetween sized for receiving the apparatus therein in the collapsed configuration, the sheath including a slit extending at least partially between the sheath proximal and distal ends to facilitate removal of the sheath from around the apparatus.

13. The system of claim 12, further comprising a trocar received through the lumen of the introducer sheath to facilitate advancing the sheath directly through tissue, the trocar being removable from the sheath after introducing the sheath into the cavity.

14. A brachytherapy treatment apparatus, comprising:
an elongate core member comprising a proximal end and a distal end sized for introduction into a tract through tissue, and the core member defining a longitudinal axis between the proximal and distal ends;
a distal hub coupled to the distal end of the core member;
a proximal hub on the proximal end of the core member, at least one of the proximal hub and the distal hub movable axially relative to the other of the proximal hub and the distal hub;
a guide member on the core member disposed between the proximal and distal hubs; and
a plurality of elongate members coupled to the proximal and distal hubs and extending between the proximal and distal ends of the core member, the elongate members comprising pathways for receiving a source of radiation therealong, the elongate members movable between a collapsed configuration wherein intermediate regions of the elongate members are received in respective recesses in the guide member for introduction through a tissue tract to a target location, and an expanded configuration when one of the proximal and distal hubs is directed towards the other of the proximal and distal hubs, the intermediate regions moving radially out of the respective recesses as the elongate members are directed towards the expanded configuration.

15. The apparatus of claim 14, wherein the elongate members are received in the recesses in the collapsed configuration such that the elongate members do not extend substantially parallel to the longitudinal axis.

16. The apparatus of claim 14, wherein the elongate members are received in the recesses in the collapsed configuration such that the elongate members are arched in the collapsed configuration.

17. The apparatus of claim 14, wherein the recesses comprise side walls that prevent substantial lateral motion of the elongate members while the intermediate regions are received in the recesses.

18. The apparatus of claim 14, wherein the recesses comprise grooves that extend substantially parallel to the longitudinal axis.

19. A method for brachytherapy treatment of tissue within a body, comprising:
creating a tract through tissue to a target location adjacent to a cavity;
advancing a distal portion of an elongate body through the tract into the target location with the distal portion in a collapsed configuration, the distal portion comprising a plurality of elongate members disposed around an elongate core member with intermediate regions of the elongate members being received in respective recesses in a guide member between proximal and distal hubs on the core member at the distal portion in the collapsed configuration;
directing the distal portion to an expanded configuration at the target location wherein the elongate members expand away from a central axis and the intermediate regions exit the respective recesses; and
delivering radiation to the target location via the distal portion to treat tissue at the target location.

20. A brachytherapy treatment apparatus, comprising:
an elongate core member comprising a proximal end, and a distal end sized for introduction into a tract through tissue, the core member defining a longitudinal axis between the proximal and distal ends;
a distal hub coupled to the distal end of the core member;
a proximal hub on the proximal end of the core member, at least one of the proximal hub and the distal hub movable axially relative to the other of the proximal hub and the distal hub;
a plurality of elongate members coupled to the proximal and distal hubs and extending between the proximal and distal ends of the core member, the elongate members comprising pathways for receiving a source of radiation therealong, the elongate members movable between a collapsed configuration for introduction through a tissue tract to a target location, and an expanded configuration when one of the proximal and distal hubs is directed towards the other of the proximal and distal hubs; and
a guide member on the core member disposed between the proximal and distal ends, the guide member having a size such that intermediate regions of the elongate members contact the guide member in the collapsed configuration such that the elongate members do not extend substantially parallel to the longitudinal axis.

21. The apparatus of claim 20, wherein the elongate members are received in respective recesses in the guide member in the collapsed configuration.

22. The apparatus of claim 20, wherein the elongate members are arched in the collapsed configuration.

23. A method for brachytherapy treatment of tissue within a body, comprising:
creating a tract through tissue to a target location adjacent to a cavity;
advancing a distal portion of an elongate body through the tract into the target location with the distal portion in a collapsed configuration, the distal portion comprising a plurality of elongate members disposed around an elongate core member with intermediate regions of the elongate members being received in respective recesses in a guide member on the core member in the collapsed configuration;
directing the distal portion to an expanded configuration at the target location wherein the elongate members expand away from a central axis and the intermediate regions exit the respective recesses; and
delivering radiation to the target location via the distal portion to treat tissue at the target location, wherein the elongate members are arched in the collapsed configuration, the elongate members arching further in the expanded configuration.

* * * * *